United States Patent
Mishra et al.

(10) Patent No.: US 9,475,842 B2
(45) Date of Patent: Oct. 25, 2016

(54) HEXADEPSIPEPTIDE ANALOGUES AS ANTICANCER COMPOUNDS

(71) Applicant: PIRAMAL ENTERPRISES LIMITED, Mumbai (IN)

(72) Inventors: Prabhu Dutt Mishra, Mumbai (IN); Sreekumar Sankaranarayanan Eyyammadichiyl, Mumbai (IN); Saji David George, Thane (IN); Shailendra Sonawane, Mumbai (IN); Narayan Subhash Chakor, Mumbai (IN); Abhijit Roychowdhury, Mumbai (IN); Rajiv Sharma, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 14/399,321

(22) PCT Filed: May 6, 2013

(86) PCT No.: PCT/IB2013/053613
§ 371 (c)(1),
(2) Date: Nov. 6, 2014

(87) PCT Pub. No.: WO2013/168075
PCT Pub. Date: Nov. 14, 2013

(65) Prior Publication Data
US 2015/0080312 A1 Mar. 19, 2015

Related U.S. Application Data

(60) Provisional application No. 61/643,814, filed on May 7, 2012.

(51) Int. Cl.
| | | |
|---|---|---|
| *A61K 38/00* | (2006.01) | |
| *A61P 35/00* | (2006.01) | |
| *C07K 7/64* | (2006.01) | |
| *C07K 11/02* | (2006.01) | |

(52) U.S. Cl.
CPC ............... *C07K 7/64* (2013.01); *C07K 11/02* (2013.01); *A61K 38/00* (2013.01)

(58) Field of Classification Search
CPC .............. A61K 38/00; A61K 38/15
See application file for complete search history.

(56) References Cited

PUBLICATIONS

Akikiho et al., JPH11269090, published on Oct. 5, 1999.*
Machine Translated, Akikiho et al., JPH11269090, published on Oct. 5, 1999.*

* cited by examiner

*Primary Examiner* — Hasan Ahmed
*Assistant Examiner* — Kaipeen Yang
(74) *Attorney, Agent, or Firm* — Ladas & Parry LLP

(57) ABSTRACT

This invention relates to an isolated compound of Formula (1)

Formula (1)

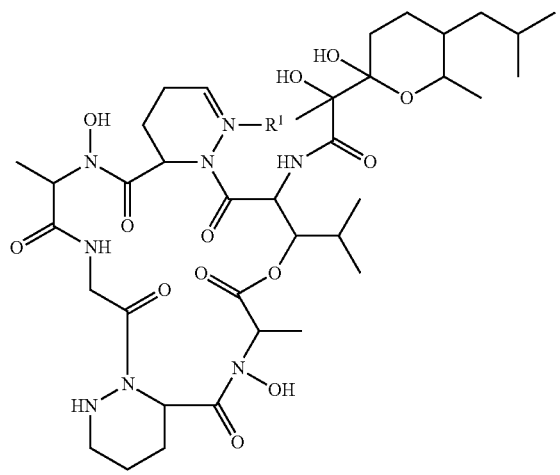

or derivatives or pharmaceutically acceptable salts thereof. The invention also includes all isomeric and tautomeric forms of the compound of Formula (1) or the derivatives thereof. The present invention further relates to processes for the production of the compound of Formula (1) by fermentation of the fungal strain of Actinomycetes (PM0895172/MTCC 684), pharmaceutical compositions comprising the compound of Formula (1) as the active ingredient; and use of the compounds or composition containing them in the treatment of cancer.

16 Claims, 5 Drawing Sheets

A- Control
B- Compound of Formula (1a) in 0.0003 µM concentration
C- Compound of Formula (1a) in 0.003 µM concentration
D- Compound of Formula (1a) in 0.01 µM concentration

HEXADEPSIPEPTIDE ANALOGUES AS ANTICANCER COMPOUNDS

RELATED APPLICATION INFORMATION

This application is a 371 of International Application PCT/IB2013/053613 filed 6 May 2013, which was published in the English language on 14 Nov. 2013 with International Publication Number WO 2013/168075 A1, and which claims priority from U.S. Provisional Application No. 61/643,814 filed 7 May 2012, the content of which is incorporated herein by reference.

FIELD OF THE INVENTION

The present invention relates to a compound of Formula (1) (as described herein), a pharmaceutically acceptable salt or a derivative thereof. The present invention further relates to a process for production of the compound of Formula (1) from the isolated microorganism belonging to Actinomycetes strain (PM0895172/MTCC 5684). The present invention also relates to a pharmaceutical composition comprising compound of Formula (1), or a pharmaceutically acceptable salt or a derivative thereof as an active ingredient; and use thereof for the treatment of cancer.

BACKGROUND OF THE INVENTION

Cancer is a generic term for a large group of diseases caused by uncontrolled growth and spread of cells that can affect any part of the body. Currently numerous treatment options are available for cancer, including chemotherapy, surgery and radiation for localised disease or a combination of said treatments. The choice of therapy depends upon the location of cancer and also the extent to which the cancer has spread at the time of diagnosis. Chemotherapy is one of the most common forms of treatment for cancer which involves use of anticancer drugs that can destroy the cancer cells. Despite continuing advances in the treatment regimens for cancer, this disease still remains one of the leading causes of death in the world, most probably for the reason that the available treatment options are associated with undesirable side effects and limited efficacy. Hence, new anticancer agents/drugs showing clinical benefits for treating cancer are needed.

There are reports of anticancer compounds such as taxol, vincristine, torreyanic acid, and camptothecin from natural resources (Natural Product Communications, 2009, 4 (11), 1513).

The marine environment, covering seventy percent of the earth's surface and ninety five percent of its tropical biosphere represents thirty four of the thirty six phyla of life and provides a fascinating variety of biodiversity exceeding that of the terrestrial environment (Life Sciences, 2005, 78, 442-453). Marine natural product bioprospecting, which is exploration, extraction and screening of biological diversity and indigeneous knowledge for commercially valuable genetic and biochemical resources, has yielded a considerable number of drug candidates (Drug Discovery Today, 2003, 8 (12), 536-544).

There have been reports of discovery of numerous pharmaceutical agents involving screening of natural products from marine organisms and microorganisms. Examples of anticancer agents originating from a marine source include citarabine, bryostatin-1, aplidine, dolastatin 10 and ET-743 (Current Opinion in Pharmacology, 2001, 1, 364-369).

A number of hexadepsipeptides are reported in the art. For example, JP09040559 discloses hexadepsipeptide class of compounds having anti-inflammatory activity which are effective against both allergic and non-allergic inflammations.

Considering that many therapeutically active compounds have been obtained from natural sources, it would be prudent to explore this area of research to obtain new compounds that can be effectively used in the treatment of diseases like cancer. The inventors of the present patent application directed their efforts to provide a novel compound which finds use in the treatment of cancer. Also provided are the methods to produce this compound by fermentation and further, effecting chemical modifications of the compound of Formula (1) to obtain its derivatives.

SUMMARY OF THE INVENTION

The present invention relates to a compound designated herein as the compound of Formula (1) (as described herein).

The present invention relates to isomeric form, tautomeric form of the compound of Formula (1) or a pharmaceutically acceptable salt or a derivative thereof.

According to the present invention the compound of Formula (1) is the compound of Formula (1a) or the compound of Formula (1b).

According to the present invention, the derivatives of the compound of Formula (1) are encompassed in the compound of Formula (1c).

The present invention also relates to a purified compound of Formula (1), isolated from the culture broth obtained by fermentation of marine actinomycetes strain (PM0895172/MTCC 5684) or one of its variants or mutants. Accordingly, the compound of the present invention is an isolated compound of Formula (1).

The present invention also relates to processes for the production of the compound of Formula (1), and/or its isomer or its tautomer from the marine actinomycetes strain (PM0895172/MTCC 5684).

The present invention further relates to a process for the isolation of microorganism belonging to Actinomycetes strain (PM0895172/MTCC 5684) which on cultivation produces the compound of Formula (1), or its isomer or tautomer.

The compound of Formula (1), or its isomer or tautomer, or a pharmaceutically acceptable salt or a derivative thereof, is useful for the treatment of cancer.

The present invention relates to a method for the treatment of cancer in a subject comprising administering to the subject a therapeutically effective amount of a compound of Formula (1), or an isomer or a tautomer or a pharmaceutically acceptable salt or a derivative thereof.

The present invention also relates to a pharmaceutical composition comprising the compound of Formula (1) or an isomer or a tautomer or a pharmaceutically acceptable salt or a derivative thereof, as an active ingredient in association with at least one pharmaceutically acceptable excipient, a carrier or a vehicle.

DETAILED DESCRIPTION OF THE INVENTION

Figure 1:
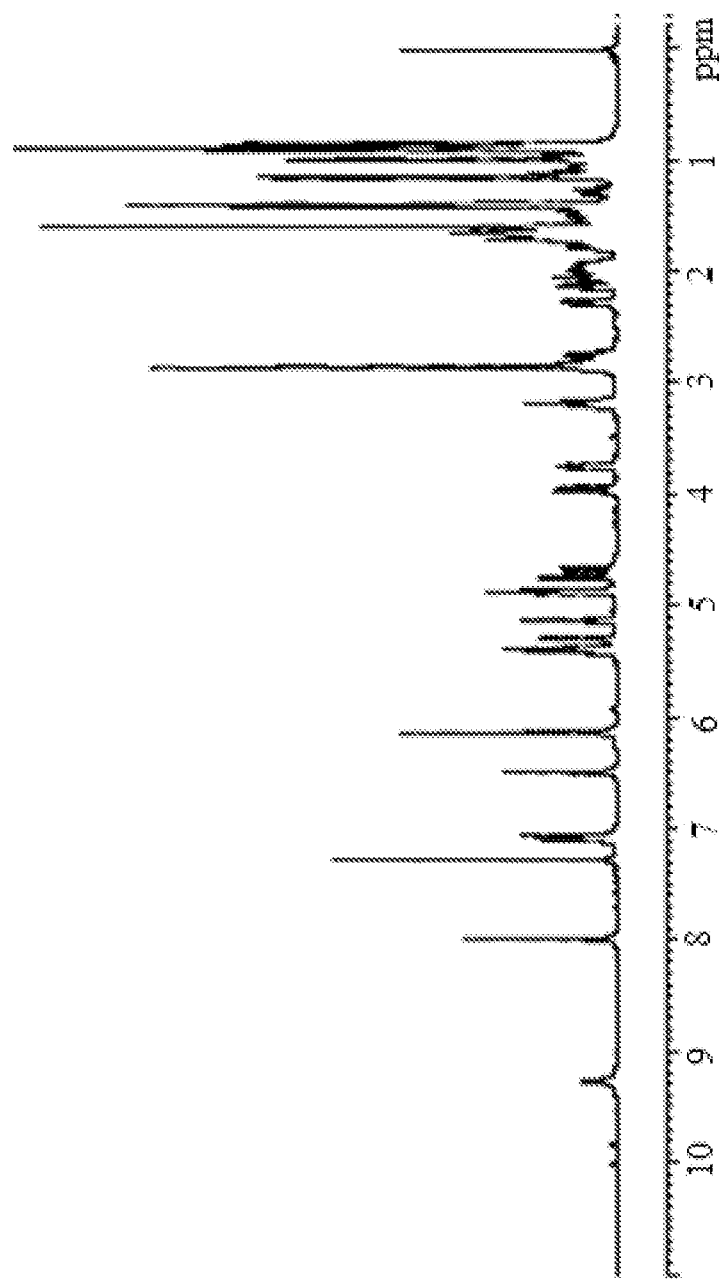
FIG. 1 illustrates $^1$H NMR (CDCl$_3$; 500 MHz; Instrument: Bruker) spectrum of the compound of Formula (1a).

The present invention provides a compound of Formula (1) represented as follows:

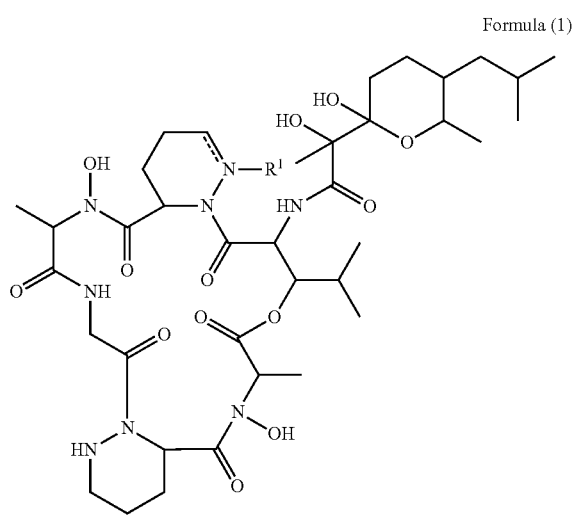

Formula (1)

wherein in the compound of Formula (1), when the bond ╌╌╌ represents a single bond and R$^1$ is H; the compound is referred to as the compound of Formula (1a); and when the bond ╌╌╌ is a double bond and R$^1$ is absent; the compound is referred to as the compound of Formula (1b). Accordingly, the compound of Formula (1) is a compound of Formula (1a) (wherein the bond ╌╌╌ represents a single bond and R$_1$ is H) or the compound of Formula (1b) (wherein the bond ╌╌╌ is a double bond and R$^1$ is absent) or a mixture thereof.

The compound of Formula (1) belongs to hexadepsipeptide class of compounds.

The compound of Formula (1a) and the compound of Formula (1b) can be characterized by any one or more of the physico-chemical and spectral properties, such as high performance liquid chromatography (HPLC), high resolution mass spectrum (HR MS), infra red (IR) and nuclear magnetic resonance (NMR) spectroscopic data as discussed herein below.

According to an aspect of the invention, the compound of Formula (1) is the compound of Formula (1a) which has molecular formula C$_{37}$H$_{62}$N$_8$O$_{13}$ and molecular weight of 826.9.

Compound of Formula (1a) is represented as follows:

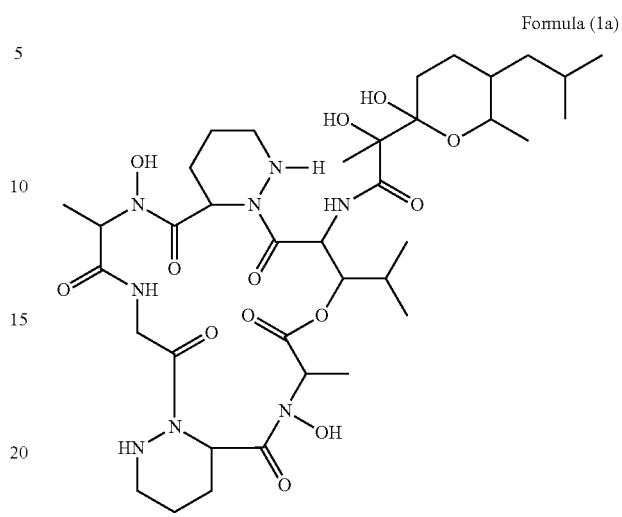

Formula (1a)

The chemical name of the compound of Formula (1a) is N-(6,18-dihydroxy-22-isopropyl-7,19-dimethyl-5,8,11,17,20,24-hexaoxotetracosa hydrodipyridazino[6,1-f:6',1'-o][1,4,7,10,13,16]oxapentaazacyclononadecin-23-yl)-2-hydroxy-2-(2-hydroxy-5-isobutyl-6-methyltetrahydro-2H-pyran-2-yl)propanamide.

According to an aspect of the invention, the compound of Formula (1) is the compound of Formula (1b) which has molecular formula C$_{37}$H$_{60}$N$_8$O$_{13}$ and molecular weight of 824.4.

Compound of Formula (1b) is represented as follows:

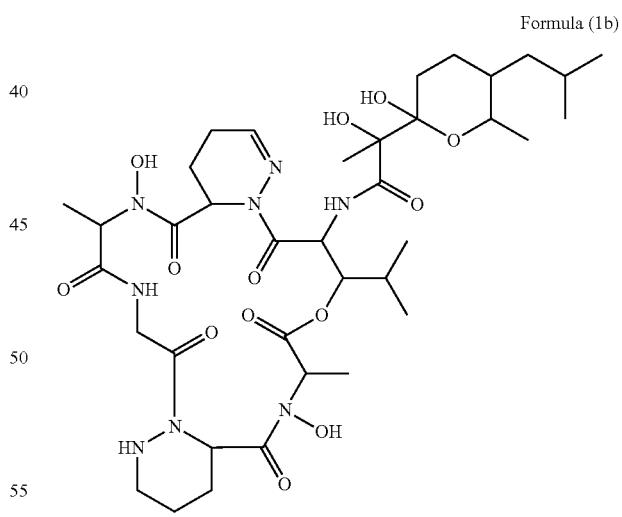

Formula (1b)

The chemical name of the compound of Formula (1b) is N-(6,18-dihydroxy-22-isopropyl-7,19-dimethyl-5,8,11,17,20,24-hexaoxo-3,4,4a,5,6,7,8,9, 10,11,13,14,15, 16,16a, 17,18,19,20,22,23,24-docosahydrodipyridazino[6,1-f:6',1'-o][1,4,7,10, 13,16]oxapentaaza cyclononadecin-23-yl)-2-hydroxy-2-(2-hydroxy-5-isobutyl-6-methyltetra hydro-2H-pyran-2-yl)propanamide.

The microorganism which can be used for the production of the compound of Formula (1), is an Actinomycetes strain (PM0895172/MTCC 5684), herein after referred to as culture no. PM0895172 which is isolated from deep marine sediment collected from the offshore region of Mumbai, Maharashtra, India.

One aspect of the present invention provides a process for the production of the compound of Formula (1) from the culture no. PM0895172, comprising the steps of:
a) growing the culture no. PM0895172 or one of its variants or mutants under submerged aerobic conditions in nutrient medium containing one or more sources of carbon and one or more sources of nitrogen and nutrient inorganic salts and/or trace elements to obtain a culture broth containing the compound of Formula (1);
b) isolating the compound of Formula (1) from the culture broth; and
c) purifying the compound of Formula (1).

The compound of Formula (1) produced according to the above process may be the compound of Formula (1a) or the compound of Formula (1b).

In an embodiment, the culture broth in step (a) contains a mixture of the compound of Formula (1a) and compound of Formula (1b).

In an embodiment, in step (b) of the process, the compound of Formula (1) is the compound of Formula (1a).

In an embodiment, in step (b) of the process, the compound of Formula (1) is the compound of Formula (1b).

In an embodiment, in step (c) of the process, the compound of Formula (1) is the compound of Formula (1a).

In an embodiment, in step (c) of the process, the compound of Formula (1) is the compound of Formula (1b).

In an embodiment, the present invention provides a process for the production of the compound of Formula (1a) from the culture no. PM0895172, comprising the steps of:
a) growing the culture no. PM0895172 or one of its variants or mutants under submerged aerobic conditions in nutrient medium containing one or more sources of carbon and one or more sources of nitrogen and nutrient inorganic salts and/or trace elements to obtain a culture broth containing a mixture of the compound of Formula (1a) and compound of Formula (1b);
b) isolating the compound of Formula (1a) from the culture broth; and
c) purifying the compound of Formula (1a).

In another embodiment, the present invention provides a process for the production of the compound of Formula (1b) from the culture no. PM0895172, comprising the steps of:
a) growing the culture no. PM0895172 or one of its variants or mutants under submerged aerobic conditions in nutrient medium containing one or more sources of carbon and one or more sources of nitrogen and nutrient inorganic salts and/or trace elements to obtain a culture broth containing a mixture of the compound of Formula (1a) and compound of Formula (1b);
b) isolating the compound of Formula (1b) from the culture broth; and
c) purifying the compound of Formula (1b).

The step (c) in any one of the processes as described above involves purification of the compound of Formula (1) and is carried out by using purification procedures generally used in the related art.

The compound of Formula (1), particularly the compound of Formula (1a) and the compound of Formula (1b) produced according to the process of the present invention are substantially pure compounds. Thus, the compound of Formula (1), particularly the compound of Formula (1a) or the compound of Formula (1b) is an isolated pure compound.

Typically, the compound of Formula (1a) and the compound of Formula (1b) are purified by column chromatographic techniques.

As used herein, the term "mutant" refers to an organism or a cell in which one or more genes in the genome has/have been modified, with the gene, or the genes, which is/are responsible for the ability of the organism to produce the compound according to the invention. Such mutants can be produced, in a manner known per se, using physical means, for example irradiation, as with ultraviolet rays or X-rays, or chemical mutagens.

As used herein, the term "variant" refers to an individual organism that is recognizably different from an arbitrary standard type in that species.

The term "whole broth" may be used interchangeably with the terms "nutrient broth", "culture broth" or "fermented broth".

The term "mammal" as used herein, refers to human as well as non-human mammals, including but not limited to, cows, horses, pigs, dogs and cats. The term "mammal" may be used interchangeably with the term "patient" or "subject".

The term "active ingredient" or "active compound" may be used interchangeably and as used herein, said term(s) refers to the compound of Formula (1) or the compound of Formula (1a) or the compound of Formula (1b) or an isomer or a tautomer or a pharmaceutically acceptable salt or a derivative thereof. In the context of the present invention, the term "active ingredient" or "active compound" also refers to the compounds of Formula (1c) which encompass the derivatives of the compounds of Formula (1) as described herein.

The term "compound of Formula (1)" includes the compound of Formula (1a) or the compound of Formula (1b) or a mixture thereof; and an isomer, a tautomer, or a pharmaceutically acceptable salt thereof.

The term "compound of Formula (1c)" includes the derivatives of the compound of Formula (1) including that of the compound of Formula (1a) or the compound of Formula (1b) or an isomer, a tautomer, or a pharmaceutically acceptable salt thereof.

The term "substantially pure" as used herein, means that the compound of Formula (1), particularly the compound of Formula (1a) or the compound of Formula (1b) or an isomer thereof is sufficiently pure such that further purification would not detectably alter its physical and chemical properties as well as enzymatic and biological activities, of the compound. Compound of Formula (1) can be purified substantially by following the methods known to those skilled in the art.

As used herein the term "therapeutically effective amount" in reference to the treatment of cancer (as listed herein) using the compound of Formula (1), particularly the compound of Formula (1a) or the compound of Formula (1b) or a pharmaceutically acceptable salt or a derivative (the compound of Formula (1c) (as described herein)) thereof, refers to an amount capable of invoking one or more of the following effects in a subject receiving the compound of the present invention: (i) inhibition, to some extent, of tumor growth, including, slowing down and complete growth arrest; (ii) reduction in the number of tumor cells; (iii) reduction in tumor size; (iv) inhibition (i.e., reduction, slowing down or complete stopping) of tumor cell infiltration into peripheral organs; (v) inhibition (i.e., reduction, slowing down or complete stopping) of metastasis; (vi) enhancement of anti-tumor immune response, which may, but does not have to, result in the regression of the tumor; and/or (vii) relief, to some extent, of one or more symptoms associated with the cancer being treated.

The term "pharmaceutically acceptable salt(s)", as used herein, means those salts of the compound(s) of the invention including the compound of Formula (1), particularly the compound of Formula (1a) or the compound of Formula (1b), and the derivatives (the compound of Formula (1c)) thereof that are safe and effective in mammals and that possess the desired biological activity. Pharmaceutically acceptable acid addition salts include, but are not limited to, hydrochloride, hydrobromide, hydroiodide, nitrate, sulfate, phosphate, acetate, lactate, salicylate, citrate, tartrate, ascorbate, succinate, maleate, fumarate, formate, benzoate, glutamate, methanesulfonate, benzensulfonate, or p-toluenesulfonate salts. Suitable base addition salts include, but are not limited to, calcium, lithium, magnesium, potassium, sodium, or zinc salts.

Preliminary identification of culture no. PM0895172, from which the compound of Formula (1) is produced, was performed by examination of its colony characteristics. Microscopic studies on the strain of isolated culture no. PM0895172 were carried out on modified actinomycetes isolation agar medium. The observations were made after 20-22 days of incubation at 20° C. to 30° C., till colonies were observed. Culture no. PM0895172 has been identified as a marine actinomycetes strain.

Culture no. PM0895172 has been deposited with Microbial Type Culture Collection (MTCC), Institute of Microbial Technology, Sector 39-A, Chandigarh -160 036, India, a World Intellectual Property Organization (WIPO) recognized International Depository Authority (IDA) and has been given the accession number MTCC 5684.

In addition to the specific microorganism described herein, it should be understood that mutants of PM0895172, such as those produced by the use of chemical or physical mutagens including X-rays, U.V. rays etc. and organisms whose genetic makeup has been modified by molecular biology techniques, may also be cultivated to produce the compound of Formula (1).

The screening for suitable mutants and variants which can produce the compound according to the invention can be confirmed by HPLC, NMR, IR, MS and/or determination of biological activity of the active compounds accumulated in the culture broth, for example by testing the compounds for anticancer activity or by a combination thereof.

The medium and/or nutrient medium used for isolation and cultivation of culture no. PM0895172, which produces the compound of Formula (1), preferably contains sources of carbon, nitrogen and nutrient inorganic salts. The carbon sources are, for example, one or more of starch, glucose, sucrose, dextrin, fructose, molasses, glycerol, lactose, or galactose. A preferred carbon source is glucose. The sources of nitrogen are, for example, one or more of soyabean meal, peanut meal, yeast extract, beef extract, peptone, malt extract, corn steep liquor, gelatin, or casamino acids. Preferred nitrogen source is peptone and yeast extract. The nutrient inorganic salts are, for example, one or more of sodium chloride, potassium chloride, calcium chloride, manganese chloride, magnesium chloride, strontium chloride, cobalt chloride, potassium bromide, sodium fluoride, sodium hydrogen phosphate, potassium hydrogen phosphate, dipotassium hydrogen phosphate, disodium phosphate, calcium carbonate, sodium bicarbonate, sodium silicate, sodium nitrate, ammonium nitrate, potassium nitrate, sodium sulphate, ammonium sulphate, ammonium heptamolybdate, ferric citrate, copper sulphate, magnesium sulphate, ferrous sulphate, zinc sulphate or boric acid. Sodium chloride and calcium chloride are preferred.

The maintenance of culture no. PM0895172 may be carried out at a temperature ranging from 24° C. to 32° C. Typically, culture no. PM0895172 is maintained at 27° C.-29° C. The well-grown cultures may be preserved in the refrigerator at 4° C.-8° C.

Seed culture cultivation of culture no. PM0895172 may be carried out at a temperature ranging from 27° C. to 33° C. and a pH of about 5.5 to 8.5, for 60-80 hours at 210-260 rpm (revolutions per minute). Typically, culture no. PM0895172 seed is cultivated at 29° C.-31° C. and a pH of about 6.5-7.5, for 70-74 hours at 230-250 rpm.

The production of the compound of Formula (1) may be carried out by cultivating culture no. PM0895172 by fermentation in shake flasks at a temperature ranging from 27° C. to 33° C. and a pH of about 5.5 to 8.5, for 80-110 hours at 200-250 rpm. Typically, culture no. PM0895172 is cultivated at 29° C.-31° C. and pH 6.5-7.5, for 90-100 hours at 210-230 rpm.

The production of the compound of Formula (1) may be carried out by cultivating culture no. PM0895172 by fermentation in a fermenter at a temperature ranging from 27° C. to 33° C. and a pH of about 5.5 to 8.5, for 20-40 hours at 40-70 rpm and 200-300 lpm (liters per minute) aeration. Typically, culture no. PM0895172 is cultivated at 28° C.-31° C. and pH 6.5-7.5, for 20-30 hours at 50-60 rpm and 240-260 lpm aeration.

The production of the compound of Formula (1) can be carried out by cultivating culture no. PM0895172 in a suitable nutrient broth under conditions described herein, preferably under submerged aerobic conditions, for example in shake flasks. The progress of fermentation and production of the compound of Formula (1) can be detected by high performance liquid chromatography (HPLC) and by measuring the bioactivity of the culture broth by testing against different cancer cell lines.

Fermentation is a process of growing microorganisms for the production of various chemical or pharmaceutical compounds. Microbes are normally incubated under specific conditions in the presence of nutrients. Whole broth is obtained after completing the process of fermentation. The whole broth is subjected to centrifugation which results in the formation of cell mass and culture filtrate, which can be processed further by processes, described herein.

The compound of Formula (1) present in the culture broth, can be in the form of a mixture of the compound of Formula (1a) and the compound of Formula (1b) and the said compound of Formula (1a) or the compound of Formula (1b) can be isolated using different extraction methods and chromatographic techniques.

The compound of Formula (1), particularly the compound of Formula (1a) or the compound of Formula (1b), can be recovered from the culture filtrate by extraction with a water immiscible solvent such as petroleum ether, dichloromethane, chloroform, ethyl acetate, diethyl ether or butanol, or by hydrophobic interaction chromatography using polymeric resins such as "Diaion HP-20®" (Mitsubishi Chemical Industries Limited, Japan), "Amberlite XAD®" (Rohm and Haas Industries, USA) or adsorption on activated charcoal. These techniques may be used repeatedly, alone or in combination.

The compound of Formula (1), particularly the compound of Formula (1a) or the compound of Formula (1b), can be recovered from the cell mass by extraction with a water miscible solvent such as methanol, acetone, acetonitrile, n-propanol, or iso-propanol or with a water immiscible solvent such as petroleum ether, dichloromethane, chloroform, ethyl acetate or butanol.

Alternatively, the whole broth is extracted with a solvent selected from petroleum ether, dichloromethane, chloroform, ethyl acetate, methanol, acetone, acetonitrile, n-propanol, iso-propanol, or butanol.

Typically, the compound of Formula (1) is extracted from the whole broth or culture broth using ethyl acetate as the solvent. Concentration of the extract gives the active crude material containing a mixture of compound of Formula (1a) and compound of Formula (1b).

The compound of Formula (1), particularly the compound of Formula (1a) or the compound of Formula (1b) in accordance with the present invention can be recovered from the crude material by fractionation using any of the following techniques: normal phase chromatography (using alumina or silica gel as stationary phase; eluents such as petroleum ether, ethyl acetate, dichloromethane, acetone, chloroform, methanol, isopropyl alcohol, or combinations thereof); reverse phase chromatography (using reverse phase silica gel such as dimethyloctadecylsilylsilica gel (RP-18) or dimethyloctylsilyl silica gel (RP-8) as stationary phase; and eluents such as water, buffers (for example, phosphate, acetate, citrate (pH 2-8)), and organic solvents (for example methanol, acetonitrile, acetone, tetrahydrofuran, or combinations of these solvents); gel permeation chromatography (using resins such as Sephadex LH-20® (Pharmacia Chemical Industries, Sweden), TSKgel® Toyopearl HW (TosoHaas, Tosoh Corporation, Japan) in the solvents such as methanol, chloroform, acetone, ethyl acetate, or their combinations); or by counter-current chromatography (using a biphasic eluent system made up of two or more solvents such as water, methanol, ethanol, isopropanol, n-propanol, tetrahydrofuran, acetone, acetonitrile, methylene chloride, chloroform, ethyl acetate, petroleum ether, benzene, and toluene). These techniques may be used repeatedly, alone or in combination. A typical method is chromatography over normal phase silica gel and reverse phase silica gel such as RP-18.

As used herein, the term "isomer" is a general term used for all the isomers of the compound of Formula (1) that differ only in the orientation of their atoms in space. The term isomer includes mirror image isomers (enantiomers), mixtures of mirror image isomers (racemates, racemic mixtures) and isomers of compounds with more than one chiral center that are not mirror images of one another (diastereoisomers). The compound of the present invention may have asymmetric centers and occur as racemates, racemic mixtures, individual diastereoisomers, or enantiomers, or may exist as geometric isomers, with all isomeric forms of said compound being included in the present invention.

As used herein, the term "tautomer" refers to the coexistence of two (or more) compounds that differ from each other only in the position of one (or more) mobile atoms and in electron distribution, for example, keto-enol tautomer.

The compound of Formula (1), an isomer or a tautomer thereof can be converted into their pharmaceutically acceptable salts or a derivative which are all contemplated by the present invention.

The pharmaceutically acceptable salts of the compounds of Formula (1) can be prepared by standard procedures known to one skilled in the art, for example, salts like sodium and potassium salts can be prepared by treating the compound of Formula (1), or an isomer, or a tautomer or a derivative thereof, with a suitable sodium or potassium base, for example sodium hydroxide, potassium hydroxide and the like. Similarly, salts like hydrochloride and sulphate salts, can be prepared by treating the compound of Formula (1), or an isomer, a tautomer, or a derivative thereof, with a suitable acid, for example hydrochloric acid, sulphuric acid and the like.

All the derivatives of the compounds of Formula (1), particularly of the compound of Formula (1a) or the compound of Formula (1b), are encompassed within the scope of the present invention. The derivatives of the compound of Formula (1), particularly that of the compound of Formula (1a) or the compound of Formula (1b), of particular interest according to the present invention are those wherein one or more of the amino group and the hydroxy group, particularly N-hydroxy groups of the compound of Formula (1), particularly that of the compound of Formula (1a) or the compound of Formula (1b), are derivatised.

Accordingly, in one aspect of the present invention there are provided derivatives of the compound of Formula (1), which are represented by the following Formula (1c),

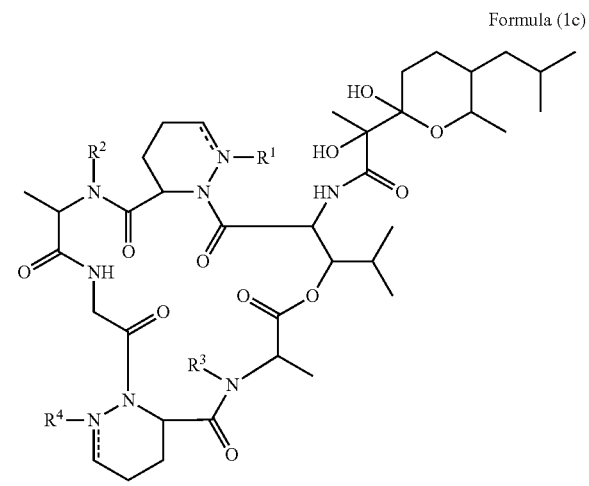

Formula (1c)

wherein,
$R^1$ and $R^4$ independently represent H or absent;
$R^2$ and $R^3$ are independently selected from H, hydroxy, —O($C_1$-$C_6$)alkyl and —OC(O)($C_1$-$C_6$)alkyl;
▬▬▬ represents a single bond or double bond;
wherein,
($C_1$-$C_6$)alkyl is unsubstituted or substituted with one or more groups independently selected from halogen, hydroxy, —O($C_1$-$C_6$)alkyl, nitro, cyano, —COOH, —$NH_2$, —NH ($C_1$-$C_6$)alkyl, —N[($C_1$-$C_6$)alkyl]$_2$, —NHC(O)O($C_1$-$C_6$) alkyl, —NHC(O)O($C_1$-$C_6$)alkyl($C_6$-$C_{10}$)aryl, —NH-PEG or ($C_6$-$C_{10}$)aryl;
($C_6$-$C_{10}$)aryl is unsubstituted or substituted with one or more groups independently selected from halogen, halo($C_1$-$C_6$)alkyl, hydroxy, cyano, nitro, ($C_1$-$C_6$)alkyl, —O($C_1$-$C_6$) alkyl, —COOH and —$NH_2$;
and PEG is polyethylene glycol selected from O,O'-bis[2-(N-succinimidyl-succinylamino)ethyl]polyethylene glycol (α,ω-bis-NHS-PEG), methyl-PEG-NHS ester (MS (PEG)n where n is 24), and a branched trimethyl and succinimide ester derivative of polyethylene glycol (TMS (PEG)n, wherein n is 12);
with a proviso that if both $R^2$ and $R^3$ are hydroxy, then $R^1$ and $R^4$ are absent and ▬▬▬ represents a double bond;
and all isomeric and tautomeric forms or pharmaceutically acceptable salts thereof.

It will be understood that "substitution," "substituted" or "substituted with" means that one or more hydrogens of the specified moiety are replaced with a suitable substituent and includes the implicit proviso that such substitution is in accordance with permitted valence of the substituted atom and the substituent, and results in a stable compound.

The term "$(C_1\text{-}C_6)$alkyl" or "alkyl", as used herein either alone or as part of another group refers to unsubstituted or substituted straight or branched chain hydrocarbons containing 1 to 6 carbons such as methyl, ethyl, propyl, isopropyl, butyl, t-butyl, isobutyl, pentyl and hexyl. The substituted alkyl refers to a $(C_1\text{-}C_6)$alkyl substituted with one or more groups selected from, but not limited to, halogen, hydroxy, —O$(C_1\text{-}C_6)$alkyl, nitro, cyano, —COOH, —NH$_2$, —NH$(C_1\text{-}C_6)$alkyl, —N[$(C_1\text{-}C_6)$alkyl]$_2$, —NHC(O)O$(C_1\text{-}C_6)$alkyl, —NHC(O)O$(C_1\text{-}C_6)$alkyl$(C_6\text{-}C_{10})$aryl, —NH-PEG or $(C_6\text{-}C_{10})$aryl.

As used herein, the term "$(C_6\text{-}C_{10})$aryl" or "aryl" refers to a monocyclic or bicyclic hydrocarbon ring system having up to ten ring carbon atoms, wherein at least one carbocyclic ring is having a π electron system. Examples of $(C_6\text{-}C_{10})$aryl ring systems include, but not limited to, phenyl or naphthyl. Unless indicated otherwise, aryl group may be unsubstituted or substituted with one or more groups independently selected from, but not limited to, halogen, halo$(C_1\text{-}C_6)$alkyl, hydroxy, cyano, nitro, $(C_1\text{-}C_6)$alkyl, —O$(C_1\text{-}C_6)$alkyl, —COOH and —NH$_2$.

As used herein, the term "—O$(C_1\text{-}C_6)$alkyl" or "alkoxy" refers to unsubstituted or substituted $(C_1\text{-}C_6)$alkyl radical having an oxygen attached thereto. Representative alkoxy groups include, but not limited to, methoxy, ethoxy, n-propoxy, 1-methylethoxy, n-butoxy, 1-methylpropoxy, 2-methylpropoxy or 1,1-dimethylethoxy. The substituted alkoxy group refers to an —O$(C_1\text{-}C_6)$alkyl group in which the alkyl is substituted with one or more groups selected from, but not limited to, halogen, hydroxy, —O$(C_1\text{-}C_6)$alkyl, nitro, cyano, —COOH, —NH$_2$, —NH$(C_1\text{-}C_6)$alkyl, —N[$(C_1\text{-}C_6)$alkyl]$_2$, —NHC(O)O$(C_1\text{-}C_6)$alkyl, —NHC(O)O$(C_1\text{-}C_6)$alkyl$(C_6\text{-}C_{10})$aryl, —NH-PEG or $(C_6\text{-}C_{10})$aryl.

As used herein, the term "halo$(C_1\text{-}C_6)$alkyl" or "haloalkyl" refers to radicals wherein one or more of the hydrogen atoms of the alkyl group are substituted with one or more halogens. A monohaloalkyl radical, for example, may have one chlorine, bromine, iodine or fluorine atom. Dihalo- and polyhaloalkyl radicals may have two or more of the same or different halogen atoms. Examples of "halo$(C_1\text{-}C_6)$alkyl" or "haloalkyl" include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoro methyl, difluoroethyl or difluoropropyl.

As used herein, the term "halogen" refers to fluorine, chlorine, bromine and iodine.

As used herein, the term "PEG" refers to polyethylene glycol polymer. PEGs are non-toxic, non-immunogenic, non-antigenic and are highly soluble in water. PEG is commercially available in a variety of molecular weights based on the number of repeating subunits of ethylene oxide (i.e. —OCH$_2$CH$_2$—) within the molecule. For example, PEG is available from commercial suppliers such as Sigma-Aldrich Co. LLC or NOF Corporation. Some examples of PEGs are, but not limited to: (a) O,O'-bis[2-(N-succinimidyl-succinyl amino) ethyl]polyethylene glycol (α,ω-bis-NHS-PEG), molecular weight in the range of 2000 Da to 10,000 Da, which is structurally presented below:

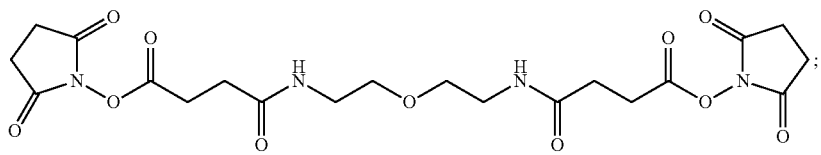 [SMILES: O=C(CCC(=O)ON1C(=O)CCC1=O)NCCOCCNC(=O)CCC(=O)ON1C(=O)CCC1=O]

(b) methyl-PEG-NHS ester (MS(PEG)n where n is 24), molecular weight 1214.39 Da, which is structurally presented below;

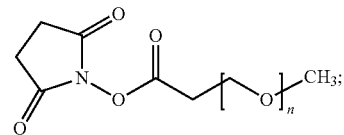

and;

(c) a branched trimethyl and succinimide ester derivative of polyethylene glycol (TMS(PEG)n, wherein n is 12, molecular weight 2420.80 Da. Typically, PEG having molecular weight in the range of 1000 to 20,000 Da is preferred for use in the preparation of PEG conjugates of the compounds as described herein.

In the context of the present invention, the terms "compounds of Formula (1c)", "derivatives of the compound of Formula (1)", or "derivative(s) of Formula (1c)" are used interchangeably and each of these terms refer to the derivatives of the compound of Formula (1) represented by Formula (1c); and an isomer, a tautomer, or a pharmaceutically acceptable salt thereof.

According to one embodiment, the present invention provides the compounds of Formula (1c),
wherein,
$R^1$ and $R^4$ is H;
$R^2$ is —O$(C_1\text{-}C_6)$alkyl or —OC(O)$(C_1\text{-}C_6)$alkyl;
$R^3$ is hydroxy or —O$(C_1\text{-}C_6)$alkyl;
wherein, $(C_1\text{-}C_6)$alkyl is unsubstituted or substituted with —NH$_2$, —NHC(O)O$(C_1\text{-}C_6)$alkyl$(C_6\text{-}C_{10})$aryl or —NH-PEG;
and all isomeric and tautomeric forms or pharmaceutically acceptable salts thereof.

According to another embodiment, the present invention provides the compounds of Formula (1c),
wherein,
$R^1$ and $R^4$ independently represent H or absent;
$R^2$ and $R^3$ is independently selected from H and hydroxy;
----- represents a single bond or double bond;
with a proviso that if both $R^2$ and $R^3$ are hydroxy, then $R^1$ and $R^4$ are absent and ----- represents a double bond;
and all isomeric and tautomeric forms or pharmaceutically acceptable salts thereof.

Representative compounds of Formula (1c) encompassed in accordance with the present invention include:
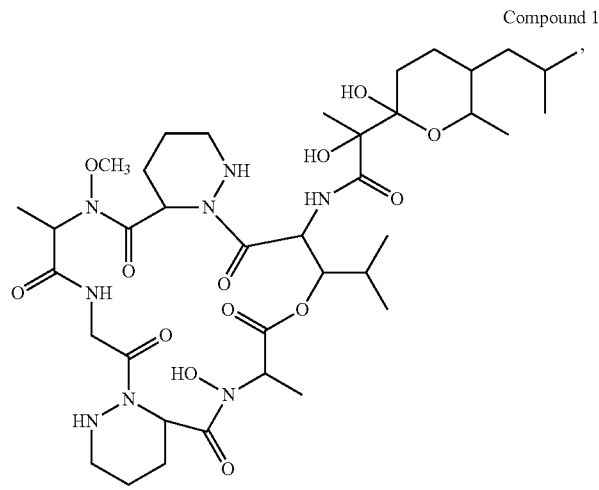
Compound 1
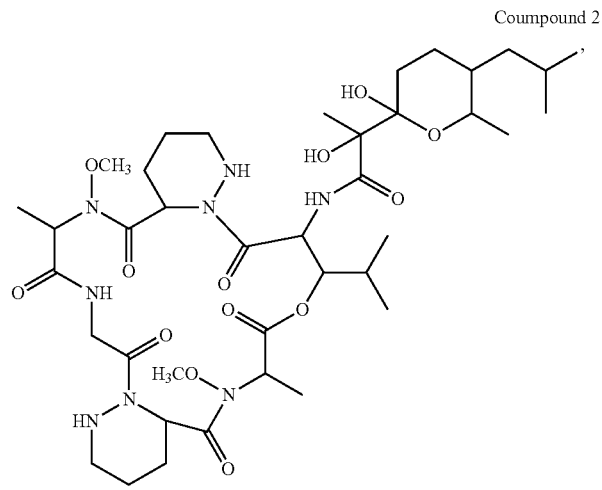
Coumpound 2
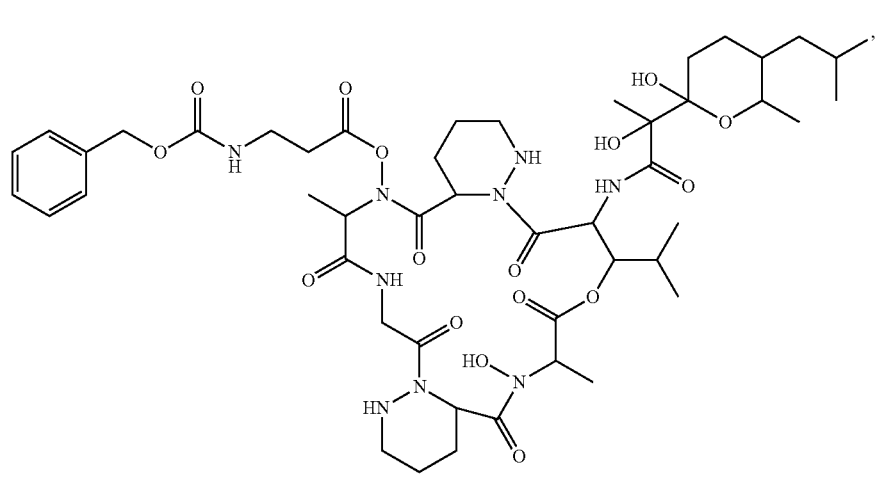
Compound 3
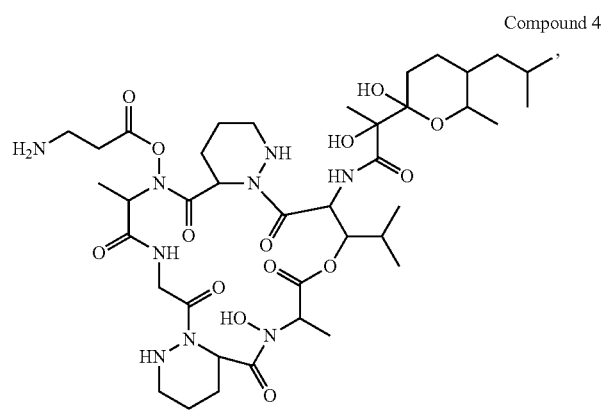
Compound 4
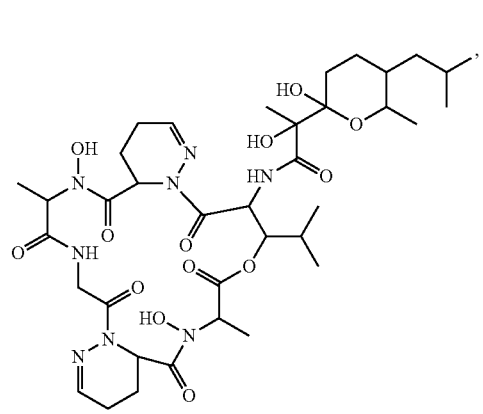
Compound 5

-continued

Compound 6

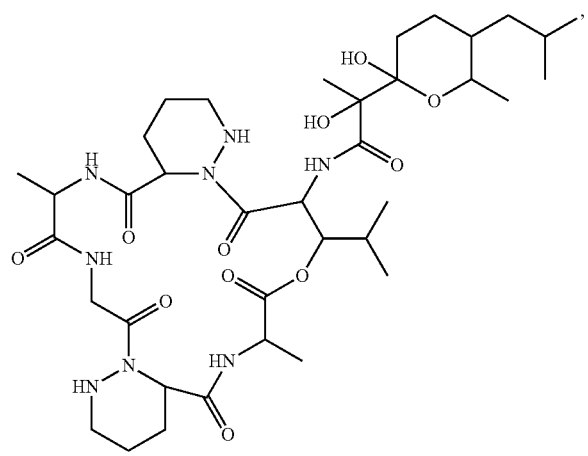

Compound 7

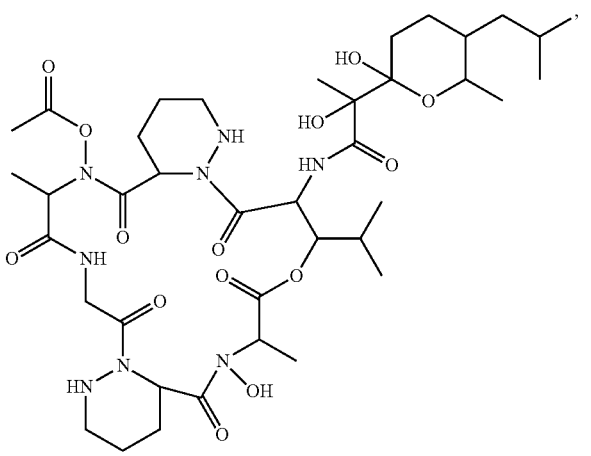

Compound 8

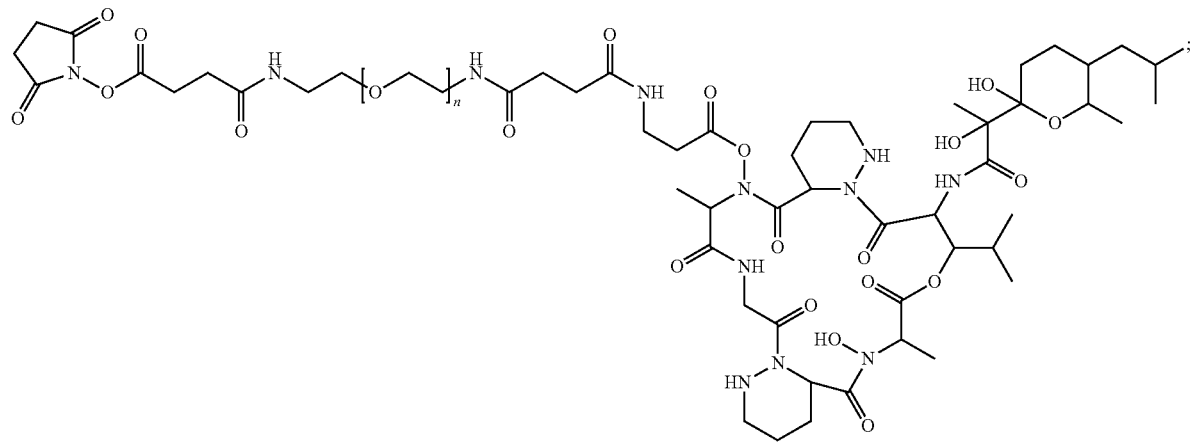

and all isomeric and tautomeric forms or pharmaceutically acceptable salts thereof.

Derivatives of the compound of Formula (1), represented by the Formula (1c), may be prepared by the methods known in the art. Reagents employed in the processes for the preparation of the compounds of Formula (1c) may be commercially available or may be prepared by processes known in the art.

The compounds of Formula (1c) wherein $R^1$ and $R^4$ are H; and $R^2$ and $R^3$ are independently selected from hydroxy and —O($C_1$-$C_6$)alkyl, wherein at least one of $R^2$ and $R^3$ is —O($C_1$-$C_6$)alkyl, can be prepared by reacting the compound of Formula (1), which is the compound of Formula (1a) in an alcohol selected from methanol, ethanol, propanol or butanol in combination with toluene or benzene, with alkylating reagents such as trimethylsilyldiazomethane in an organic solvent such as hexane or toluene, at a temperature ranging from −5° C. to 5° C., for 1 hr to 5 hours. Compounds 1 and 2 are prepared by this method.

The compounds of Formula (1c) wherein $R^1$ and $R^4$ are H; and $R^2$ and $R^3$ are independently selected from hydroxy and —OC(O)($C_1$-$C_6$)alkyl such that at least one of $R^2$ and $R^3$ is —OC(O)($C_1$-$C_6$)alkyl; wherein the ($C_1$-$C_6$)alkyl is substituted with —NHC(O)O($C_1$-$C_6$)alkyl($C_6$-$C_{10}$)aryl, can be prepared by reacting compound of Formula (1), which is the compound of Formula (1a), in solvents such as tetrahydrofuran (THF), dichloromethane (DCM), or dimethylformamide (DMF), with reagents such as N-benzyloxycarbonyl-L-alanine (Cbz alanine) or N-(9-fluorenylmethoxycarbonyl)-L-alanine (Fmoc alanine), in the presence of a coupling agent such as benzotriazol-1-yl-oxytripyrrolidinophosphonium hexafluorophosphate (Py-POP), (benzotriazol-1-yloxy)tris(dimethylamino) phosphor niumhexafluorophosphate(BOP), N,N'-dicyclohexylcarbodiimide (DCC) or propane phosphonic acid anhydride (T3P), and a base such as N,N-diisopropylethylamine (DIPEA), triethylamine, or 4-dimethylaminopyridine (DMAP), at a temperature ranging from −5° C. to 5° C., for 1 hr to 20 hours. Compound 3 is prepared by this method. The compound thus obtained may be deprotected by catalytic reduction using catalyst such as Pd/C or Pt/C, in a solvent such as methanol, ethnanol, ethyl acetate or THF, in acidic condition created by using an acid such as dilute HCl, to obtain the compound of Formula (1c) wherein $R^2$ and $R^3$ are independently selected from hydroxy and —OC(O)($C_1$-$C_6$)alkyl such that at least one of $R^2$ and $R^3$ is —OC(O)($C_1$-$C_6$)alkyl; wherein the ($C_1$-$C_6$)alkyl is substituted with —NH$_2$. Compound 4 is prepared by this method.

The compounds of Formula (1c) wherein $R^1$ and $R^4$ are H; and $R^2$ and $R^3$ are independently selected from hydroxy and —OC(O)($C_1$-$C_6$)alkyl such that at least one of $R^2$ and $R^3$ is —OC(O)($C_1$-$C_6$)alkyl; wherein the ($C_1$-$C_6$)alkyl is substituted with —NH$_2$, can be used for pegylation, by dissolving the said compound in an organic solvent such as DCM, methanol or DMF, in presence of a base such as triethylamine or DIPEA, and adding a polyethylene glycol (PEG) polymer such as O,O'-bis[2-(N-succinimidyl-succinylamino) ethyl]polyethylene glycol (α,ω-bis-NHS-PEG) or methyl-PEG-NHS ester, and stirring at a temperature ranging from 25° C. to 35° C., for 10 hrs-20 hrs, to obtain the compound of Formula (1c) wherein $R^2$ and $R^3$ is independently selected from hydroxy and —OC(O)($C_1$-$C_6$)alkyl such that at least one of $R^2$ and $R^3$ is —OC(O)($C_1$-$C_6$)alkyl; wherein the ($C_1$-$C_6$)alkyl is substituted with —NH-PEG. Compound 8 is prepared by this method.

The compound of Formula (1), can be oxidized to remove the hydrogen at the $R^1$ and $R^4$ positions, by using a reagent such m-chloroperbenzoic acid in an organic solvent selected from dichloromethane or dichloroethane, at a temperature ranging from 25° C. to 35° C., for 10-20 hours to obtain the compound of Formula (1c) wherein $R^1$ and $R^4$ are absent and $R^2$ and $R^3$ are hydroxy. Compound 5 is prepared by this method.

The N-hydroxy groups of the compound of Formula (1), can be converted to NH (deoxygenation) by adding the compound of Formula (1) in an organic solvent selected from methanol, ethanol or DMF, to a solution of reagent such as bis(cyclopentadienyl)titanium(IV) dichloride and activated zinc in solvent such as THF, DCM or DMF, and stirring at a temperature ranging from –5° C. to –50° C., for 0.1 hr to 1 hr, to obtain the compound of Formula (1c) wherein $R^1$ and $R^4$ are H or absent and $R^2$ and $R^3$ are H. Compound 6 is prepared by this method.

The acyl derivatives of N-hydroxy groups of the compound of Formula (1), can be prepared by reacting the compound of Formula (1) in solvents such as dichloromethane, pyridine or dichloroethane with reagents such as acetyl chloride or acetic anhydride, in presence of a base such as pyridine, TEA or DMAP, at a temperature ranging from –5° C. to 30° C., for 1 hr to 5 hrs, to obtain the compound of Formula (1c) wherein $R^2$ and $R^3$ is independently selected from hydroxy and —OC(O)($C_1$-$C_6$)alkyl such that at least one of $R^2$ and $R^3$ is —OC(O)($C_1$-$C_6$)alkyl. Compound 7 is prepared by this method.

The compounds of Formula (1c) which are the derivatives of the compound of Formula (1) can be optionally converted to their pharmaceutically acceptable salts.

The compound of Formula (1) or a pharmaceutically acceptable salt or a derivative of Formula (1c) thereof has anticancer activity. This has been demonstrated by testing representative compounds of the present invention including that of the compound(s) of Formula (1), Formula (1a), Formula (1b) and Formula (1c) respectively; against a wide range of cancer cells.

The compound of Formula (1), or an isomer or a tautomer or a pharmaceutically acceptable salt or a derivative of Formula (1c) thereof, can be administered to a subject in need thereof, as a pharmaceutical and in the form of a pharmaceutical composition. The compound of Formula (1) or an isomer or a tautomer or a pharmaceutically acceptable salt or a derivative of Formula (1c) thereof, can be administered to a patient who is diagnosed having cancer.

Accordingly, the present invention also relates to the use of the compound of Formula (1), particularly of the compound of Formula (1a) or the compound of Formula (1b), or an isomer or a tautomer or a pharmaceutically acceptable salt or a derivative of Formula (1c) thereof, for the manufacture of a medicament for the treatment of cancer.

The present invention further relates to a pharmaceutical composition comprising a therapeutically effective amount of the compound of Formula (1) or an isomer or a tautomer or a pharmaceutically acceptable salt or a derivative of Formula (1c) thereof, and a pharmaceutically acceptable excipient or a carrier. The pharmaceutical composition is provided for use in the treatment of cancer. The therapeutically effective amount of the compound of Formula (1), or its stereoisomer, or its tautomer or its pharmaceutically acceptable salt or its derivative of Formula (1c) as the active ingredient in the pharmaceutical preparations may range from about 0.01 mg to 1000 mg; or may range from about 0.1 mg to 750 mg; or may range from about 0.5 mg to 500 mg; or may range from about 1 mg to 250 mg.

The compounds of the present invention including the compound of Formula (1), or an isomer or a tautomer or a pharmaceutically acceptable salt or a derivative of Formula (1c) thereof, find use in the treatment of cancers. Compounds of present invention are used to reduce, inhibit, or diminish the proliferation of tumor cells, and can provide for the reduction of the size of a tumor. Representative cancers that can be treated by the compounds of the present invention include but are not limited to leukemia, lung cancer, brain tumors, non-Hodgkin's lymphoma, Hodgkin's disease, liver cancer, kidney cancer, bladder cancer, cancer of urinary tract, breast cancer, head and neck cancer, endometrial cancer, lymphoma, melanoma, cervical cancer, thyroid cancer, gastric cancer, germ cell tumor, cholangiocarcinoma, extracranial cancer, sarcoma, mesothelioma, malignant fibrous histiocytoma of bone, retinoblastoma, esophageal cancer, multiple myeloma, pancreatic cancer, ependymoma, neuroblastoma, skin cancer, ovarian cancer, recurrent ovarian cancer, prostate cancer, testicular cancer, colorectal cancer, lymphoproliferative disease, refractory multiple myeloma, resistant multiple myeloma or myeloproliferative disorder.

According to an embodiment of the present invention, the cancer is selected from acute lymphocytic leukemia, acute myeloid leukemia, adult acute myeloid leukemia, acute lymphoblastic leukemia, chronic lymphocytic leukemia, chronic myeloid leukemia, hairy cell leukemia, non-small-cell lung cancer, small-cell lung cancer, brain stem glioma, glioblastoma, astrocytoma including cerebellar astrocytoma and cerebral astrocytoma, visual pathway glioma, hypothalamic glioma, supratentorial primitive neuroectodermal, pineal tumors, medulloblastoma, primary central nervous system lymphoma, mantle cell lymphoma, Hodgkin's disease, hepatocellular carcinoma, renal cell carcinoma, Wilms' tumor, bladder cancer, cancer of urinary tract, Ewing's sarcoma family of tumors, osteosarcoma, rhabdomyosarcoma, soft tissue sarcomas, mesothelioma, breast cancer, endometrial cancer, oral cancer, melanoma, cervical cancer, thyroid cancer, gastric cancer, germ cell tumor, cholangiocarcinoma, extracranial cancer, malignant fibrous histiocytoma of bone, retinoblastoma, esophageal cancer, multiple myeloma, pancreatic cancer, ependymoma, neuroblastoma, skin cancer, ovarian cancer, recurrent ovarian cancer, prostate cancer, testicular cancer, colorectal cancer, lymphoproliferative disease, refractory multiple myeloma, resistant multiple myeloma or myeloproliferative disorder, among others.

According to another embodiment of the present invention, the cancer is selected from acute lymphocytic leukemia, acute myeloid leukemia, adult acute myeloid leukemia, acute lymphoblastic leukemia, chronic lymphocytic leukemia, chronic myeloid leukemia, hairy cell leukemia, non-small-cell lung cancer, small-cell lung cancer, brain stem glioma, glioblastoma, astrocytoma including cerebellar astrocytoma and cerebral astrocytoma, visual pathway glioma, pineal tumors, medulloblastoma, primary central nervous system lymphoma, mantle cell lymphoma, Hodgkin's disease, hepatocellular carcinoma, renal cell carcinoma, bladder cancer, cancer of urinary tract, osteosarcoma, breast cancer, endometrial cancer, oral cancer, melanoma, cervical cancer, thyroid cancer, gastric cancer, malignant fibrous histiocytoma of bone, retinoblastoma, esophageal cancer, multiple myeloma, pancreatic cancer, neuroblastoma, skin cancer, ovarian cancer, prostate cancer, testicular cancer, colorectal cancer, lymphoproliferative disease or myeloproliferative disorder, among others.

According to further embodiment of the present invention, the cancer is selected from acute lymphocytic leukemia, acute myeloid leukemia, adult acute myeloid leukemia, acute lymphoblastic leukemia, chronic lymphocytic leukemia, chronic myeloid leukemia, hairy cell leukemia, non-small-cell lung cancer, small-cell lung cancer, brain stem glioma, glioblastoma, astrocytoma including cerebellar astrocytoma and cerebral astrocytoma, medulloblastoma, renal cell carcinoma, bladder cancer, cancer of urinary tract, breast cancer, oral cancer, melanoma, cervical cancer, thyroid cancer, gastric cancer, pancreatic cancer, prostate cancer or colorectal cancer, among others.

According to an embodiment, the present invention provides a method for the treatment of cancer in a subject by administering to the subject a therapeutically effective amount of a compound of Formula (1) or a derivative of Formula (1c), or an isomer or a tautomer or a pharmaceutically acceptable salt thereof.

According to another embodiment, the present invention provides a method for the treatment of cancer in a subject by administering to the subject a therapeutically effective amount of a compound of Formula (1a) or the compound of Formula (1b) or an isomer or a tautomer or a pharmaceutically acceptable salt thereof.

According to yet another embodiment, the present invention provides a method for the treatment of cancer in a subject by administering to the subject a therapeutically effective amount of a derivative of Formula (1c) or an isomer or a tautomer or a pharmaceutically acceptable salt thereof.

The compound of Formula (1) or a pharmaceutically acceptable salt or a derivative of Formula (1c) thereof; or an isomer or a tautomer or a pharmaceutically acceptable salt thereof can be administered orally, nasally, topically, subcutaneously, intramuscularly, intravenously, or by other modes of administration.

The method of administration which is suitable in a specific case depends on the type of cancer to be treated and on the stage of the cancer. Further, the method of administration can be optimized by a medical practitioner using methods known in the art.

As is customary, the dosage range which is suitable in a specific case depends on the type of cancer to be treated and on the state of the respective condition or disease. The selected dosage level can be readily determined by a skilled medical practitioner in the light of the relevant circumstances, including the condition (cancer) to be treated, the chosen route of administration depending on a number of factors, such as age, weight and physical health and response of the individual patient, pharmacokinetics, severity of the disease and the like, factors known in the medical art. Actual dosage levels of the active ingredients in the pharmaceutical composition of this present invention can be varied so as to obtain an amount of the active ingredient, which is effective to achieve the desired therapeutic response for a particular patient (subject in need of the treatment), composition, and mode of administration without being toxic to the patient.

On an average, the daily dose of the active compound (one or more of the compounds of the present invention) for a patient can range from about 0.05 mg to about 500 mg per kg, or from about 0.5 mg to about 200 mg per kg or from about 1 mg to about 100 mg per kg or any dosage range that falls within the scope of the broader dose range as indicated herein. In case of higher body weight of the subject in need of the treatment, the dose of the active compound can range from about 1 mg to about 1000 mg or from about 5 mg to about 500 mg. The desirable dose of the active compound i.e. the compounds of the present invention can be selected over a wide range. The daily dosage to be administered is selected to achieve the desired therapeutic effect in subjects being treated for cancers. If required, higher or lower daily dosages can also be administered.

Pharmaceutical compositions which contain compound of Formula (1) or an isomer or a tautomer or a pharmaceutically acceptable salt or a derivative of Formula (1c) thereof, with other pharmaceutically acceptable excipients such as, wetting agents, solubilisers such as surfactants, vehicles, tonicity agents, fillers, colorants, masking flavors, lubricants, disintegrants, diluents, binders, plasticizers, emulsifiers, ointment bases, emollients, thickening agents, polymers, lipids, oils, cosolvents, complexation agents, or buffer substances, are in the form of tablets, coated tablets, capsules, granules, powders, creams, ointments, gels, syrup, emulsions, suspensions, or solutions suitable for parenteral administration.

In one embodiment of the present invention, the pharmaceutical compositions which contain compound of Formula (1) or a derivative of Formula (1c); or an isomer or a tautomer, a pharmaceutically acceptable salt thereof, can be used in combination with one or more anticancer agents such as asparaginase, bleomycin, carboplatin, carmustine, chlorambucil, cisplatin, colaspase, cyclophosphamide, cytarabine, dacarbazine, dactinomycin, daunorubicin, doxorubicin, epirubicin, etoposide, fluorouracil, hexamethylmelamine, hydroxyurea, ifosfamide, leucovorin, lomustine, mechlorethamine, 6-mercaptopurine, mesna, methotrexate, mitomycin C, mitoxantrone, prednisolone, prednisone, procarbazine, streptozocin, tamoxifen, thioguanine, vinblastine, vincristine, vindesine, aminoglutethimide, 5-azacytidine, cladribine, busulfan, diethylstilbestrol, 2',2'-difluorodeoxycytidine, docetaxel, erythro-9-(2-hydroxy-3-nonyl) adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, teniposide, testosterone propionate, thiotepa, trimethylmelamine, uridine, vinorelbine, alsterpaullone, butyrolactone I, 2-(2-hydroxyethylamino)-6-(3-chloroanilino)-9-isopropyl purine, indirubin-3'-monoxime, kenpaullone, olomoucine, iso-olomoucine, $N^9$-isopropyl-olomoucine, purvalanol A, roscovitine, (S)-isomer roscovitine and WHI-P180 [4-(3'-hydroxyphenyl)amino-6,7-dimethoxyquinazoline]; for the treatment of cancers as described herein.

It is understood that modifications that do not substantially affect the activity of the various embodiments of this invention are included within scope of the invention disclosed herein. Accordingly, the following examples are intended to illustrate but not to limit scope of the present invention.

EXAMPLES

The following terms/symbol/abbreviations/chemical formulae are employed in the examples:

| | |
|---|---|
| L: Liter | µl: Microliter |
| ml: Milliliter | ml/min: Milliliter per Minute |
| g: Gram | rpm: Revolutions per Minute |
| mg: Milligram | ATCC: American Type Culture Collection |
| mm: Millimeter | v/v: Volume per volume |
| cm: Centimeter | DNA: Deoxy ribose Nucleic Acid |
| µ: Micron | lpm: Liters per minute |
| nm: Nanometer | hrs: Hours |
| M: Molar | mmol/mM: Millimolar |
| min: Minutes | $NaHCO_3$: Sodium bicarbonate |
| THF: Tetrahydrofuran | $Na_2SO_4$: Sodium sulphate |
| Ar: Argon | DIPEA: N,N-DiDiisopropylethylamine |
| $K_2CO_3$: Potassium carbonate | Pd/C: Palladium on carbon |
| DMF: Dimethylformamide | $TMSCHN_2$: Trimethylsilyldiazomethane |
| HCl: Hydrochloric acid | T3P: Propane phosphonic acid anhydride |
| PyBOP: Benzotriazol-1-yl-oxytripyrrolidinophosphonium hexafluorophosphate | |
| $Cp_2TiCl_2$: Bis(cyclopentadienyl)titanium(IV) dichloride | |

Example 1

Isolation of Culture No. PM0895172 from a Marine Source a) Composition of the isolation medium:

1% Peptone, 2% glucose, 0.2% calcium carbonate, 0.001% cobalt chloride.$6H_2O$, 1.5% agar; pH (at 25° C.) 7.5.

Composition of the artificial seawater (ASW): 2.46% sodium chloride, 0.067% potassium chloride, 0.136% calcium chloride, 0.629% magnesium sulphate, 0.466% magnesium chloride, 0.018% sodium bicarbonate; water.

b) Procedure

Deep sea sediment sample was collected from the offshore region of Mumbai, Maharashtra, India, and stored at −20° C. throughout the journey to NCE Research Division (Piramal LifeSciences division) of Piramal Enterprises Limited (Formerly Piramal Healthcare Limited), Goregaon (East), Mumbai, India.

Molecular approach was implemented for the isolation of uncultured marine actinomycetes from the collected sediment sample. For this, genomic DNA was isolated from the sediment samples and amplified for the presence of Polyketide Synthase (PKS) and Non-ribosomal peptide synthetases (NRPS). Culture of interest was then isolated from the sediment sample having NRPS pathway.

The sample was stored at −20° C. to −22° C. and later thawed to room temperature (25±2° C.) for isolation of the microbes. The soil sample (~2 g) was suspended in 25 ml of sterile artificial sea water (ASW) in autoclaved mortar and pestle and crushed thoroughly. 1 ml of this suspension was transferred into a test tube and vortexed for 30 seconds. The test tube was vortexed for 30 seconds. Serial dilutions up to $10^{-5}$ were prepared in sterile ASW. 100 µl of $10^{-3}$ dilution was surface spread on plate containing isolation media. The plate was incubated at room temperature (25±2° C.) till colonies were observed. After incubation for 20-22 days, the colony which appeared on this medium was streaked on petri plates containing isolation media, as mentioned above. The isolate was purified and was provided culture ID number PM0895172. The culture no. PM0895172 was thus isolated from amongst the growing microorganisms as single isolate.

Example 2

Purification of Culture No. PM0895172 a) Composition of the purification medium:

1% Peptone, 2% glucose, 0.2% calcium carbonate, 0.001% cobalt chloride.$6H_2O$, 1.5% agar; pH (at 25° C.) 7.5.

b) Procedure:

The culture no. PM0895172 was streaked on petri plate containing purification medium. The petri plate was incubated for ten days at 27° C. One of the isolated colonies from the petri plate was transferred to fresh slants containing ISP4 Agar (HiMedia, India). The slants were incubated for ten days at 27° C.

Example 3

Maintenance of Producer Strain—Culture No. PM0895172

This particular strain was maintained on slants containing ISP4 media (HiMedia, India). After dissolving the media thoroughly by heating, the resultant solution was distributed in test tubes and sterilized at 121° C. for 30 minutes. The test tubes were cooled and allowed to solidify in a slanting position. The agar slants were streaked with well grown culture no. PM0895172 by a wire loop and incubated at 27° C. to 29° C. until a good growth was observed. The well-grown cultures were stored in the refrigerator at 4° C. to 8° C.

Example 4

Fermentation of the Culture No. PM0895172 in Shake Flasks a) Composition of seed medium:

0.2% calcium carbonate, 0.5% sodium chloride, 0.5% corn steep liquor, 0.75% peptone, 1.5% glucose, 0.75% yeast extract; demineralized water; pH 7.

b) Procedure:

50 ml of the above seed medium was distributed in 500 ml capacity erlenmeyer flasks and autoclaved at 121° C. for 30 minutes. The flasks were cooled to room temperature (25±2° C.) and each flask was inoculated with a loopful of the well-grown producing strain (culture no. PM895172) on the slant and shaken on a rotary shaker for 72 hours at 230 rpm to 250 rpm at 30° C. (±1° C.) to give seed culture.

c) Composition of the production medium:

1% Peptone, 2% glucose, 0.2% calcium carbonate, 0.001% cobalt chloride.$6H_2O$, 1.5% agar and pH (at 25° C.) 7.5.

d) Procedure:

100 ml of the production media in 500 ml capacity Erlenmeyer flasks was autoclaved at 121° C. for 30 minutes, cooled to 29° C. to 30° C. and seeded with 3% (v/v) of the seed culture mentioned in example 4b.

e) Fermentation parameters:

The production flasks were incubated on shaker at 30° C. and 220 rpm for 96 hours. The production flasks were harvested (harvest pH: 7.0 to 8.0) and the whole culture broth from each media flask was extracted with equal volume of solvent mixture [methanol: ethyl acetate (1:9)]. These harvested flasks were kept at room temperature for 4-6 hrs for extraction followed by separation of the supernatant. The supernatant was used for testing anticancer activity.

Example 5

Preparation of the Seed Culture in Shake Flasks for Fermenter Batch a) Composition of the seed medium 274(1):

Glucose 15 g, corn steep liquor 5 g, peptone 7.5 g, yeast extract 7.5 g, calcium carbonate 2 g, sodium chloride 5 g, demineralized water 1.0 L, pH 6.5-7.5 (before sterilization).

b) Procedure:

200 ml of the above medium was distributed in 1000 ml erlenmeyer flasks and autoclaved at 121° C. for 30 mins. The flasks were cooled to room temperature and each flask was inoculated with a loopful of the well-grown producing strain (PM0895172) on the slant and shaken on a rotary shaker for 70-74 hours at 230-250 rpm at 29° C.-30° C. to obtain the seed culture.

Example 6

Cultivation of the Culture No. PM0895172 in Fermenter a) Composition of the production medium:

Soya peptone 10 g, glucose 20 g, calcium carbonate 2 g, cobalt chloride 0.001 g, demineralized water 1.0 L, pH 7.0 (before sterilization).

b) Procedure:

500 L of the production medium in 1000 L fermenter along with 200 ml of desmophen as an antifoaming agent was sterilized in situ for 20 mins at 121° C., cooled to 29° C.-30° C. and seeded with 8-10 L of the seed culture obtained in example 5b.

c) Fermentation parameters:

Temperature 29° C.-30° C., tip speed 0.94 m/s, aeration 250 lpm and harvest time 24 hrs. The harvest pH of the culture broth was 6.5-7.5. The production of the active compound of Formula (1a) or compound of Formula (1b) in the fermentation broth was determined by HPLC and bioactivity was tested for anti cancer activity.

Example 7

Isolation and Characterization of the Compound of Formula (1a)

The harvested whole broth (500 L) obtained in step c) of example 6, was extracted using ethyl acetate (500 L). The organic layer was separated using disc stack separator [Alfa Laval (USA), model no LAPX404] and concentrated to obtain the crude extract (150 g).

The crude extract was processed by column chromatography (silica gel, solvent: isopropyl alcohol/chloroform). The active compound was eluted with 1-2% isopropyl alcohol in chloroform, which was concentrated to obtain the enriched compound (30 g).

This material was purified by column chromatography (RP C-18 silica gel, solvent: water/acetonitrile). The active compound got eluted with 40% acetonitrile in water, which was evaporated to obtain 2 g of the desired semi pure active compound of Formula (1) [a mixture of compound of Formula (1a) and of Formula (1b)].

Further purification was carried out by reversed phase preparative HPLC as follows:

Column: Water's X-Bridge RP-18 (250 mm×19 mm, 10μ)
Eluent: Acetonitrile:water (50:50).
Flow rate: 25 ml/min
Detection (UV): 220 nm The active peak collected was evaporated to dryness to obtain 1 g of the active compound (the compound of Formula (1a)).

Final purification of the active compound was carried out by silica gel preparative HPLC as follows:

Column: Water's sunfire silica, (150 mm×19 mm, 5μ)
Eluent: Chloroform:Methanol (98.5:1.5)
Flow rate: 15 ml/min
Detection (UV): 240 nm
Rt time: 8-9 min.

The eluate containing the active compound from repeated injections was concentrated to obtain 145 mg of pure compound of Formula (1a).

Physical and spectral properties of the compound of Formula (1a) are given in Table 1.

Analytical HPLC conditions are as follows:

Column: Kromasil RP-18 (150 mm×4.6 mm, 3.5μ)
Eluent: Gradient (10% acetonitrile to 100% acetonitrile in 20 mins against water, followed by 100% acetonitrile for additional 5 mins)
Flow rate: 1 ml/min
Detection (UV): 220 nm
Retention time: 17-18 mins (Purity>99%)

TABLE 1

Physical and spectral properties of the compound of Formula (1a)

Figure 2:
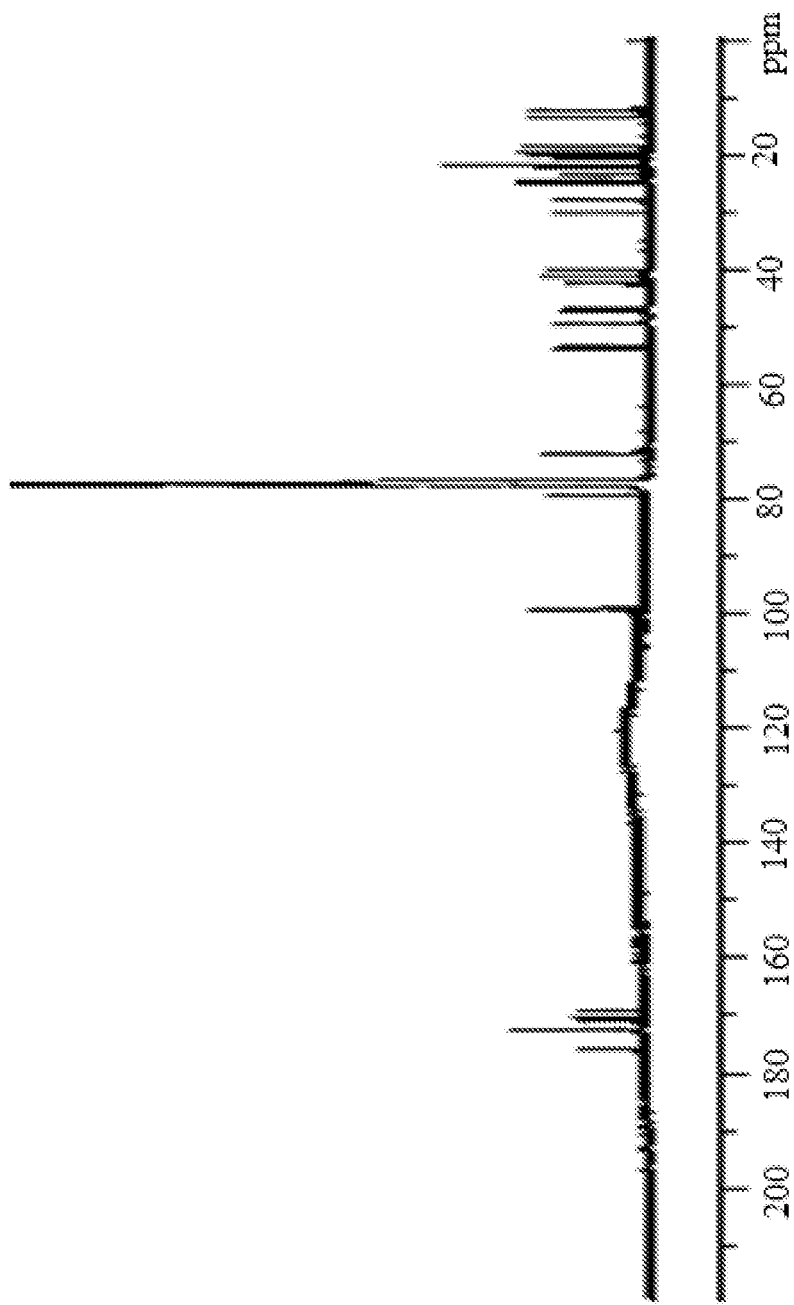
FIG. 2 illustrates $^{13}$C NMR (CDCl$_3$; 75 MHz; Instrument: Bruker) spectrum of the compound of Formula (1a).

| | |
|---|---|
| Appearance | White amorphous powder |
| Melting point | 175° C.-177° C. |
| Solubility | Soluble in chloroform, ethyl acetate and methanol; insoluble in water |
| HR MS (m/z) | 849.4287 (M + Na) |
| Molecular weight | 826.9 |
| Molecular formula | $C_{37}H_{62}N_8O_{13}$ |
| IR (KBr) | 3325, 2960, 2872, 1755, 1641, 1524, 1445, 1331, 1306, 1288 and 1254 cm$^{-1}$ |
| $^1$H NMR (500 MHz, CDCl$_3$) | δ 9.20, 8.00, 7.10, 6.90, 6.40, 6.10, 5.40, 5.38, 5.29, 5.10, 4.90, 4.80, 4.70, 4.60, 3.90, 3.70, 3.15, 2.70, 2.30, 2.10, 1.98, 1.95, 1.77, 1.71, 1.68, 1.60, 1.52, 1.40, 1.15, 1.10, 1.05, 0.98, 0.95, 0.90, 0.88 and 0.85 (as given in FIG. 1) |
| $^{13}$C NMR (75 MHz, CDCl$_3$) | δ 176.0, 172.0 (3), 171.0, 170.0, 169.0, 99.9, 78.9, 77.2, 71.7, 53.5, 52.9, 49.3, 49.0, 47.1, 46.7, 46.2, 42.2, 41.0, 39.8, 29.9, 27.4, 24.8, 24.6, 24.2, 24.1, 23.2, 21.7, 21.5 (2), 20.6, 19.9, 19.4, 18.1, 12.9 and 11.7 (as given in FIG. 2) |

Example 8

Isolation and Characterization of the Compound of Formula (1b)

The semi-pure compound obtained after RP-18 preparative HPLC in example 7 containing a mixture of that compound of Formula (1a) and compound of Formula (1b) is subjected to RP-18 preparative HPLC to obtain 15 mg of pure compound of Formula (1b). Physical and spectral properties of the compound of Formula (1b) are given in Table 2.

Analytical HPLC conditions are as follows:

Column: Kromasil RP-18 (150 mm×4.6 mm, 3.5μ)
Eluent: Gradient (10% acetonitrile to 100% acetonitrile in 20 mins against water, followed by 100% acetonitrile for additional 5 mins)
Flow rate: 1 ml/min
Detection (UV): 220 nm
Retention time: 15-17 mins (Purity>99%)

TABLE 2

Physical and spectral properties of the compound of Formula (1b)

Figure 3:
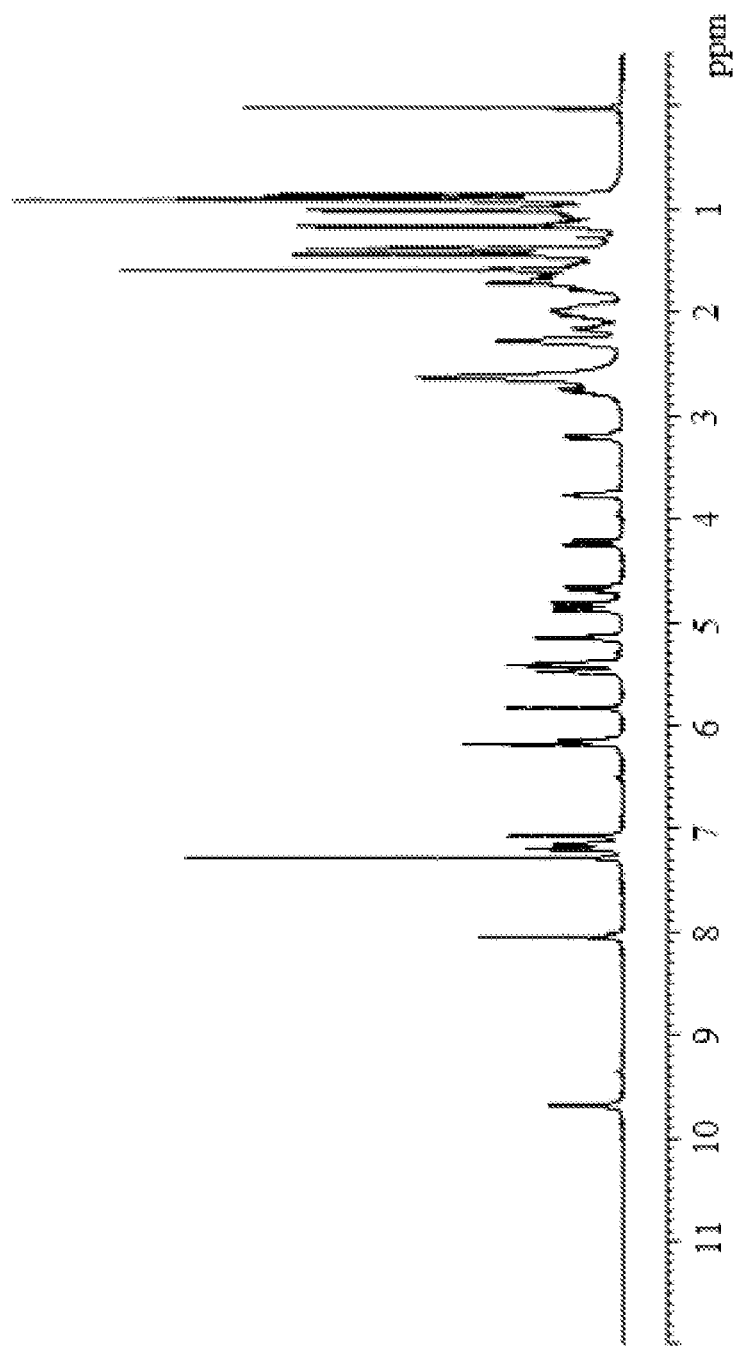
FIG. 3 illustrates $^1$H NMR (CDCl$_3$; 500 MHz; Instrument: Bruker) spectrum of the compound of Formula (1b).
Figure 4:
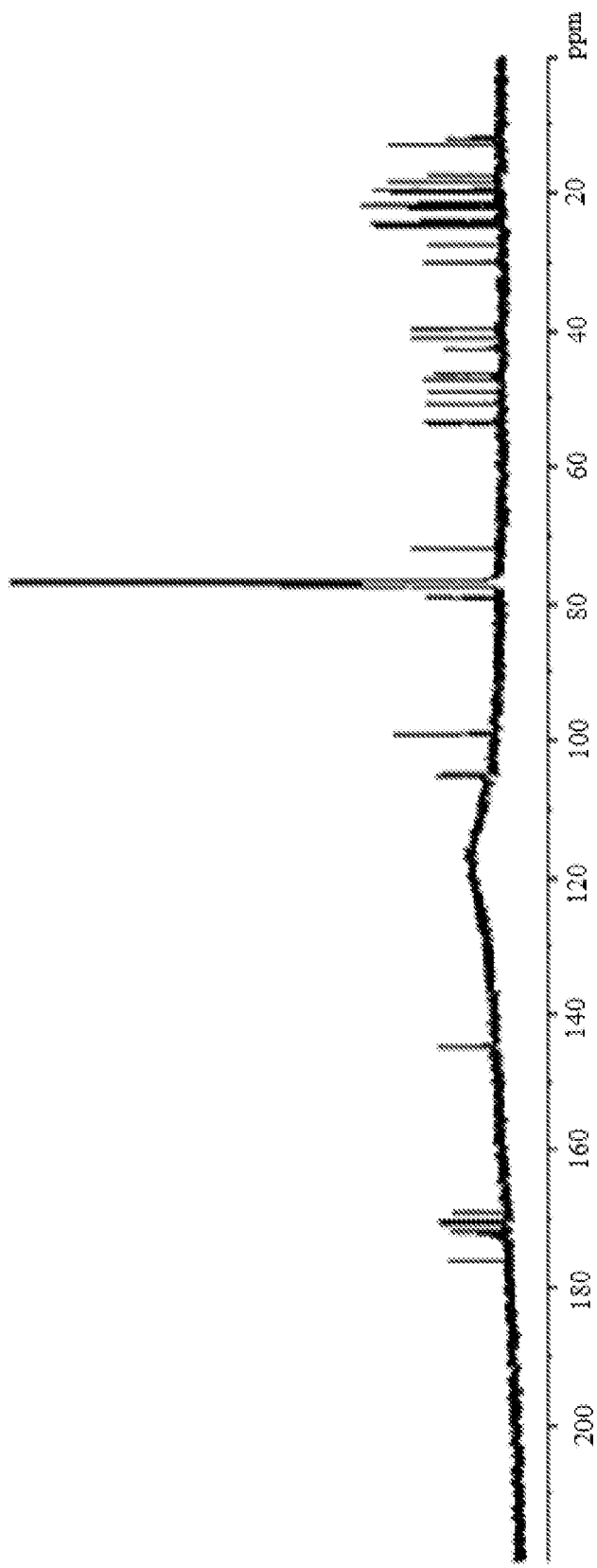
FIG. 4 illustrates $^{13}$C NMR (CDCl$_3$; 75 MHz; Instrument: Bruker) spectrum of the compound of Formula (1b).

| | |
|---|---|
| Appearance | White amorphous powder |
| Melting point | 165° C.-170° C. |
| Solubility | Soluble in chloroform, ethyl acetate and methanol and insoluble in water |
| Molecular weight | 824.4 |
| Molecular formula | $C_{37}H_{60}N_8O_{13}$ |
| IR(KBr) | 3342, 3030, 2953, 1752, 1650, 1524, 1421, 1293, 1255 and 1239 cm$^{-1}$ |
| $^1$H NMR (500 MHz, CDCl$_3$) | δ 9.20, 8.00, 7.19, 7.0, 6.18, 6.14, 5.80, 5.41, 5.39, 5.30, 5.10, 4.80 (2), 4.20, 3.70, 3.19, 2.62, 2.27, 2.10, 2.01, 1.98, 1.77, 1.71, 1.62, 1.58, 1.44, 1.40, 1.39, 1.37, 1.20, 1.10, 1.05, 0.96, 0.91, 0.90, 0.86, and 0.85 (as given in FIG. 3) |
| $^{13}$C NMR (75 MHz, CDCl$_3$) | δ 176.0, 171.8, 171.7, 170.8, 170.6, 170.3, 168.9, 144.6, 98.8, 79.0, 77.2, 71.7, 53.6, 53.5, 50.6, 49.1, 47.1, 46.4, 42.6, 41.0, 39.8, 29.9, 27.4, 24.7, 24.6, 24.2, 24.0, 22.1, 21.5, 21.4, 19.8, 19.5, 19.4, 18.1, 17.2, 12.9 and 11.8 (as given in FIG. 4) |

Example 9

Preparation of 2-hydroxy-N-(18-hydroxy-22-isopropyl-6-methoxy-7,19-dimethyl-5,8,11,17,20,24-hexaoxotetracosahydrodipyridazino[6,1-f:6',1'-o][1,4,7,10,13,16]oxapentaaza cyclononadecin-23-yl)-2-(2-hydroxy-5-isobutyl-6-methyltetrahydro-2H-pyran-2-yl) propanamide (Compound 1) and 2-hydroxy-2-(2-hydroxy-5-isobutyl-6-methyltetrahydro-2H-pyran-2-yl)-N-(22-isopropyl-6,18-dimethoxy-7,19-dimethyl-5,8,11,17,20,24-hexaoxotetracosahydrodi pyridazino[6,1-f:6',1'-o][1,4,7,10,13,16]oxapentaazacyclononadecin-23-yl)propanamide (Compound 2).

To a solution of compound of Formula (1a) [described in example 7, 20 mg, 0.024 mmol] in methanol (1 ml) and toluene (1 ml); TMSCHN$_2$ (trimethylsilyldiazomethane) (48 µl, 0.097 mmol, 2M solution in hexane) was added drop wise and the resulting reaction mixture was stirred at 0° C. for 3 hrs and then warmed to room temperature. After completion of the reaction, the solvents were removed to obtain the solid which was purified by column chromatography (silica gel, 1% methanol in dichloromethane) to obtain 5 mg of the Compound 1 and 3 mg of the Compound 2.

Compound 1: $^1$HNMR (CDCl$_3$, 300 MHz): δ 7.98, 7.10, 6.92, 6.54, 6.20, 5.52, 5.50, 5.30, 5.16, 5.14, 5.07, 4.96, 4.54, 4.51, 4.13, 4.05, 3.80, 3.18, 3.12, 2.79, 2.14, 2.04, 1.98, 1.95, 1.77, 1.71, 1.68, 1.60, 1.52, 1.45, 1.15, 1.10, 1.05, 0.98, 0.95, 0.90, 0.88, 0.85; ESI-MS: m/e 839 (M–H)$^-$.

Compound 2: $^1$HNMR (CDCl$_3$, 300 MHz): δ 7.85, 7.15, 7.10, 6.20, 5.82, 5.42, 5.38, 5.30, 5.15, 4.98, 4.80, 4.60, 4.15, 3.95, 3.85, 3.70, 3.25, 3.15, 2.85, 2.23, 2.15, 1.98, 1.95, 1.77, 1.71, 1.68, 1.65, 1.60, 1.52, 1.44, 1.15, 1.10, 1.05, 0.98, 0.95, 0.90, 0.88, 0.85; ESI-MS: m/e 853 (M–H)$^-$.

Example 10

Preparation of 18-hydroxy-23-(2-hydroxy-2-(2-hydroxy-5-isobutyl-6-methyl tetrahydro-2H-pyran-2-yl)propanamido)-22-isopropyl-7,19-dimethyl-5,8,11,17,20,24-hexaoxoicosahydrodipyridazino[6,1-f:6',1'-o][1,4,7,10,13,16]oxapentaazacyclononadecin-6(7H,13H,22H)-yl 3-(((benzyloxy)carbonyl)amino)propanoate (Compound 3).

Method I:

To a solution of the compound of Formula (1a) [described in example 7, 40 mg, 0.048 mmol] in THF (5 ml); Cbz alanine (27 mg, 0.12 mmol) and PyBOP (75 mg, 0.14 mmol) were added at 0° C. followed by drop wise addition of DIPEA (51 µl, 0.29 mmol). The resulting reaction mixture was stirred overnight at room temperature. The reaction mixture was then diluted with water (5 ml) and extracted with ethyl acetate (3×20 ml). The combined organic layers were washed with saturated NaHCO$_3$, brine, dried over anhydrous Na$_2$SO$_4$, and concentrated to obtain the crude compound which was purified by column chromatography (silica gel, 1% methanol in dichloromethane) to obtain the pure Compound 3.

Yield: 12 mg; $^1$HNMR (CDCl$_3$, 300 MHz): δ 7.90, 7.39, 7.2, 6.45, 6.34, 6.15, 5.65, 5.50, 5.38, 5.30, 5.15, 5.10, 4.90, 4.60, 4.50, 4.10, 3.85, 3.7, 3.65, 3.55, 3.4, 3.2, 3.15, 2.7, 2.6, 2.5, 2.3, 2.19, 1.98, 1.95, 1.77, 1.71, 1.68, 1.65, 1.60, 1.52, 1.44, 1.15, 1.10, 1.05, 0.98, 0.95, 0.90, 0.88, 0.85; ESI-MS: m/e 1030 (M–H)$^-$.

Method II:

To a cooled solution of Cbz alanine (67.5 mg, 0.302 mmol) in acetonitrile (20 ml, 0.121 mmol); T3P (0.216 ml, 0.363 mmol, 50 wt. % in ethyl acetate) was added under nitrogen atmosphere and stirred for 10 min. The compound of Formula (1a) [described in example 7, 100 mg, 0.121 mmol] in acetonitrile (20 ml, 0.121 mmol) was added to the above solution followed by dropwise addition of triethylamine (0.051 ml, 0.363 mmol). The resulting reaction mixture was stirred continuously for 4 hrs. After completion of the reaction, water (10 ml) was added to the reaction mixture and the reaction mixture was extracted with ethyl acetate (3×20 ml). The combined organic layers were washed with saturated NaHCO$_3$, brine and water, dried over anhydrous NaSO$_4$, and concentrated to obtain the crude compound which was purified by column chromatography (silica gel, 1-2% methanol in dichloromethane) to obtain the Compound 3. Yield: 38 mg.

Example 11

Preparation of 18-hydroxy-23-(2-hydroxy-2-(2-hydroxy-5-isobutyl-6-methyltetra hydro-2H-pyran-2-yl)propanamido)-22-isopropyl-7,19-dimethyl-5,8,11,17,20,24-hexaoxo icosahydrodipyridazino[6,1-f:6',1'-o][1,4,7,10,13,16]oxapentaazacyclononadecin-6(7H,13H,22H)-yl 3-aminopropanoate (Compound 4).

To a solution of the Compound 3, as obtained in example 10 (30 mg, 0.029 mmol) in methanol (3 ml); 1 equivalent HCl, and catalytic amount of 10% Pd/C were added and the resulting reaction mixture was stirred for 2 hr at room temperature. After completion of the reaction, the reaction mixture was filtered through celite and the filtrate was concentrated to obtain the Compound 4.

Yield: 15 mg; $^1$HNMR (DMSO-d$_6$; 300 MHz): δ 7.92, 7.30, 7.10, 6.75, 5.85, 5.45, 5.35, 5.15, 5.00, 4.85, 4.16, 3.86, 3.46, 3.10, 2.85, 2.73, 2.56, 2.15, 1.85, 1.80, 1.70, 1.68, 1.65, 1.60, 1.52, 1.44, 1.15, 1.10, 1.05, 0.98, 0.95, 0.88, 0.82, 0.80; ESI-MS: m/e 896 (M–H)$^-$.

Example 12

Preparation of N-(6,18-dihydroxy-22-isopropyl-7,19-dimethyl-5,8,11,17,20,24-hexaoxo-3,4,4a,5,6,7,8,9,10,11,15,16,16a,17,18,19,20,22,23,24-icosahydrodipyridazino[6,1-f:6',1'-o][1,4,7,10,13,16]oxapentaazacyclononadecin-23-yl)-2-hydroxy-2-(2-hydroxy-5-isobutyl-6-methyltetrahydro-2H-pyran-2-yl)propanamide (Compound 5).

To a solution of the compound of Formula (1a), as obtained in example 7 (30 mg, 0.036 mmol) in dichloromethane (6 ml); m-chloroperbenzoic acid (18 mg, 0.104 mmol) was added at 0° C. and the resulting reaction mixture was stirred overnight at room temperature. The reaction mixture was diluted with water (20 ml) and extracted with dichloromethane (3×25 ml). The combined organic layers were washed with brine, water and dried over anhydrous $Na_2SO_4$, and concentrated to obtain crude compound which was purified by column chromatography (silica gel, 5% methanol in dichloromethane to obtain the Compound 5.

Yield: 20 mg; $^1$HNMR (DMSO-$d_6$, 300 MHz): δ 10.34, 9.62, 7.84, 7.52, 7.45, 7.43, 7.07, 6.68, 6.19, 5.77, 5.64, 5.51, 5.41, 5.04, 5.02, 4.94, 4.17, 4.12, 2.20, 1.98, 1.90, 1.60, 1.51, 1.33, 1.23, 1.04, 0.90, 0.87, 0.82; ESI-MS: 846 (M+Na).

Example 13

Preparation of 2-hydroxy-2-(2-hydroxy-5-isobutyl-6-methyltetrahydro-2H-pyran-2-yl)-N-(22-isopropyl-7,19-dimethyl-5,8,11,17,20,24-hexaoxotetracosahydrodipyridazino[6,1-f:6',1'-o][1,4,7,10,13,16]oxapentaazacyclononadecin-23-yl)propanamide (Compound 6).

A clean, flame-dried, round-bottom flask equipped with a stir bar was evacuated and purged with Ar. A degassed THF solution (3 ml) of $Cp_2TiCl_2$ (193 mg, 0.774 mmol) and activated zinc (411 mg, 6.29 mmol) was stirred at room temperature under Ar for 45 min. The color of reaction mixture was changed from dark red to olive green. The reaction mixture was cooled to −30° C. and charged with a methanolic solution (3 ml) of compound of Formula (1a), as obtained in example 7 (40 mg, 0.048 mmol) dropwise over 3 min. The reaction mixture was stirred for 45 min maintaining the bath temperature between −30° C. to −10° C. The reaction mixture was warmed to room temperature and partitioned between saturated 5% $K_2CO_3$ (5 ml) and ethyl acetate (20 ml). The organic layer was removed via pipette and filtered through a whatman glass microfiber filter (type GF/F) to remove insoluble titanium salts. The aqueous layer was extracted with ethyl acetate (4×20 ml) and the organic layer was filtered through a whatman glass microfiber filter (type GF/F) after each extraction. The combined organic layers were dried over anhydrous $Na_2SO_4$, and concentrated to obtain a solid, which was purified by column chromatography (silica gel, 70% ethyl acetate in hexane) to obtain the Compound 6.

Yield: 8 mg; $^1$HNMR (DMSO-$d_6$, 300 MHz): δ 8.32, 7.78, 6.87, 6.65, 6.25, 5.75, 5.59, 5.32, 5.28, 5.21, 5.15, 4.95, 4.77, 4.73, 4.45, 4.23, 4.12, 3.94, 3.34, 2.73, 2.27, 2.18, 2.08, 1.99, 1.88, 1.63, 1.35, 1.30, 1.23, 1.04, 0.90, 0.87; ESI-MS: 817 (M+Na).

Example 14

Preparation of 18-hydroxy-23-(2-hydroxy-2-(2-hydroxy-5-isobutyl-6-methyltetra hydro-2H-pyran-2-yl)propanamido)-22-isopropyl-7,19-dimethyl-5,8,11,17,20,24-hexaoxo icosahydrodipyridazino[6,1-f:6',1'-o[]1,4,7,10,13,16]oxapentaazacyclononadecin-6(7H,13H,22H)-yl acetate (Compound 7).

To a solution of the compound of Formula (1a), as obtained in example 7 (0.050 g, 0.060 mmol) in dichloromethane (10 ml); pyridine (0.0255 ml, 0.30 mmol) was added at 0° C. and stirred for 15 min followed by addition of acetyl chloride (0.043 ml, 0.60 mmol). The resulting reaction mixture was stirred for 2 hr at room temperature. The reaction mixture was extracted with ethyl acetate (3×30 ml). The combined organic layers were washed with dilute 1% HCl (5 ml), water (10 ml), dried over anhydrous $Na_2SO_4$, and concentrated. The crude product was purified by column chromatography (2% methanol in dichloromethane) to obtain the Compound 7.

Yield: 15 mg; $^1$HNMR (CDCl$_3$, 300 MHz): δ 7.92, 7.28, 6.85, 6.45, 6.15, 5.45, 5.36, 5.20, 5.15, 4.90, 4.85, 4.65, 4.21, 3.80, 3.15, 2.35, 2.25, 2.12, 1.98, 1.95, 1.77, 1.71, 1.68, 1.60, 1.52, 1.40, 1.15, 1.05, 0.98, 0.95, 0.90, 0.88, 0.86; ESI-MS: 891 (M+Na).

Example 15

Preparation of the PEGylated Conjugate (Compound 8).

To a solution of the Compound 4 as obtained in example 11 (200 mg, 0.223 mmol) in DMF (10 ml, 0.223 mmol) was added N-ethyl-N-isopropylpropan-2-amine (135 ml, 0.779 mmol) at 0° C. and O,O'-Bis[2-(N-succinimidyl-succinyl amino) ethyl]polyethylene glycol (722 mg, 1.448 mmol) was added in one portion and the resulting reaction mixture was stirred overnight at room temperature. DMF was removed under speed vacuum at room temperature to obtain the solid which was purified through sephadex G-15 size exclusion chromatographic column.

A calibration curve was constructed using a series of concentrations of free compound of Formula (1a) in DMF and water against their absorbance at 269 nm. The concentration of the PEGylated conjugate was determined based on the content of the compound of Formula (1a) using the following formula:

Conc. of PEG conjugate=Absorbance of PEGylated conjugate−(intercept/slope)

The content of compound of Formula (1a) in the PEGylated conjugate form (Compound 8) was found to be 10%.

Example 16

Biological Evaluation of the Compound of Formula (1a):
The following terms/symbol/abbreviations/chemical formulae are employed in the pharmacological assays:

| | |
|---|---|
| $CO_2$: Carbon dioxide | EDTA: Ethylenediamine tetraacetic acid |
| mM: Milimolar | DMSO: Dimethyl Sulfoxide |
| μM: Micromolar | CCK-8: Cholecystokinin octapeptide |
| μL: Microliter | FITC: Fluorescein isothiocyanate |
| nm: Nanometer | p53: Tumor protein 53 |
| hrs: Hours | FACS: Fluorescence activated cell sorter |
| S.E: Standard error | $IC_{50}$: 50% Inhibitory concentration |
| | RT: Room temperature (25 ± 2° C.) |

In Vitro Assays
The assays were designed as in the reference, BMC Cancer, 2010, 10, 610, 1-11; the disclosure of which is incorporated by reference for the teaching of the assay.
Monolayer Assay
Step 1
Maintenance of the Cell Lines
Human tumour cell lines: Panc-1 (Pancreatic Cancer), HCT 116 (Colorectal Cancer), ACHN (Renal Cell Carcinoma), Calu-1 (Lung Carcinoma), MiaPaca2 (Pancreatic Cancer), FADU (Head and Neck Cancer), PC3 (prostate Cancer), G361 (Melanoma), MDA-MB435S (Melanoma), HeLa (Cervical Cancer) were grown in Minimal Essential Media with Eagle's Basal Salts (MEM-EBS) obtained from AMIMED (BioConcept-Switzerland). Tumour cell lines: MDA-MB231 (Breast Cancer), JURKAT (T cell leukaemia), H460 (Small Cell Lung Cancer) were cultured in RPMI 1640 (AMIMED, BioConcept, Switzerland) medium. All tumour cell lines were supplemented with 10% Foetal Bovine Serum (FBS) (GIBCO), 1% Penicillin/Streptomycin (Sigma) and 1% Anti-Anti (GIBCO) and grown in T-175 tissue culture flasks (Nunc). MCF-10A, a non-tumourigenic cell line, was cultured in Mammary Epithelial Basal Medium (MEBM) with all standard additions (Lonza, Catalog. No. CC-3150). All cells were grown in 5% $CO_2$ incubator at 37° C. Cells were passaged at 80-90% confluence. Adherent cells were trypsinised using Trypsin-EDTA (Sigma) and maintained. All cell lines were purchased from ATCC (Rockville, Md., USA).

Step 2
Sample Preparation

Compound of Formula (1a) [described in example 7] was dissolved in DMSO to give a required stock solution of 20 mM. Eight different concentrations of the compound of Formula (1a) were prepared by serial dilution of stock solution finally resulting in a (compared to the test concentration) 200-fold higher concentration. Compound of Formula (1a) was tested at the concentration of 0.0001 μM, 0.001 μM, 0.01 μM, 0.03 μM, 0.1 μM, 0.3 μM, 1 μM and 3 μM respectively. Each concentration was evaluated in triplicate.

Step 3
Assay

Method for determination of $IC_{50}$ of the compound of Formula (1a):
a) Different cancer/normal cells were seeded at a density of 3000 cells/200 μL well, in a tissue culture grade 96 well plate and allowed them to recover for 24 hrs in a humidified 5±0.2% $CO_2$ incubator at 37±0.5° C.
b) After 24 hrs, 1 μL of 200× (200 times higher than required concentration is denoted as 200×) compound of Formula (1a), dissolved in DMSO, was added to the above tissue culture plate seeded with cancer/normal cells. The final concentration of DMSO was 0.5% in wells. DMSO was used as a vehicle control.
c) After 24 hrs the plate was removed from $CO_2$ incubator and 5 μL of CCK-8 (Dojindo Molecular Technologies, Inc. USA, catalog, no. CK04-20) per well was added.
d) The plate was then placed at 37° C. for 2 hrs.
e) The absorbance was recorded at 450 nm.
f) The percent cytotoxicity was calculated using the following formula $$\text{Percent cytotoxicity} = \frac{(\text{Reading of Vehicle Control} - \text{Reading of Treated cells})}{\text{Reading of Vehicle control}} \times 100$$

The $IC_{50}$ value was estimated by visual inspection of the concentration-effect curve. For calculation of mean $IC_{50}$ values over the fourteen cell lines as tested, the geometric mean was selected.

Results are presented in Table 3, given below.

TABLE 3

$IC_{50}$ values of the compound of Formula (1a) in different cancer cell lines and normal cells

| Sr. no. | Cancer Cell lines | Type of cancer | $IC_{50}$ (μM) |
|---|---|---|---|
| 1 | Panc-1 | Pancreatic | 0.0013 ± 0.00032 |
| 2 | H460 | Non Small Cell Lung | 0.0092 ± 0.00076 |
| 3 | ACHN | Renal | 0.0071 ± 0.00064 |
| 4 | HCT116 | Colon | 0.0151 ± 0.0023 |
| 5 | Calu 1 | Lung | 0.0252 ± 0.0035 |
| 6 | MiaPaca 2 | Pancreatic | 0.0253 ± 0.0046 |
| 7 | FADU | Head and Neck | 0.0224 ± 0.0012 |
| 8 | PC3 | Prostate | 0.0052 ± 0.00041 |
| 9 | G361 | Melanoma | 0.0241 ± 0.0043 |
| 10 | MDAMB435S | Melanoma | 0.0029 ± 0.00048 |
| 11 | MDAMB231 | Breast | 0.0061 ± 0.00052 |
| 12 | HeLa | Cervical | 0.0101 ± 0.0031 |
| 13 | Jurkat | T cell leukaemia | 0.0159 ± 0.0026 |
| 14 | MCF10A | Normal Breast Epithelium | 0.0197 ± 0.0031 |

Conclusion

The in vitro study revealed that, compound of Formula (1a) showed $IC_{50}$ in the range of 0.0013 μM to 0.025 μM in different cancer cells; while in normal cells (MCF-10A) it showed an $IC_{50}$ of 0.019 μM. This data shows that the compound of Formula (1a) is active against highly proliferating cancer cell lines.

Example 17

Assay
Detection of FITC Annexin V Apoptosis:

The annexin V assay, a classical technique for detecting apoptosis, is the most commonly used method for detecting apoptosis by flow cytometry. One of the earliest features of apoptosis is the translocation of phosphatidylserine from the inner to the outer leaflet of the plasma membrane, thereby exposing phosphatidylserine to the external environment.

Annexin V (cat. no. 556420, BD Biosciences, USA) binds to phosphatidylserine exposed on the cell surface and identifies cells at an earlier stage of apoptosis.

a) HeLa cancer cells [referred to in step 1 of example 16] were seeded at a density of $0.5 \times 10^6$ cells/2000 μL well, in a tissue culture grade 96 well plate and allowed them to recover for 12 hrs in a humidified 5±0.2% $CO_2$ incubator at 37±0.5° C.
b) After 12 hrs, 5 μL of 200× (200 times higher than required concentration is represented as 200×) compound of Formula (1a) dissolved in DMSO [step 2, example 16] was added to above tissue culture plate seeded with HeLa cancer cells. The final test concentration of the compound of Formula (1a) was 0.0003 μM, 0.003 μM and 0.01 μM. The final concentration of DMSO in the wells was 0.5%.
c) After 48 hrs, the plate was removed from $CO_2$ incubator and stained for FITC annexin V using Apoptosis Detection Kit as per the manufacture instruction. (Catalogue number: 556547, BD biosciences, USA).
d) The processed cells were analyzed in BD flow cytometer for annexin V detection. The population present in M1 and M2 were determined using FACS analysis.

Figure 5:
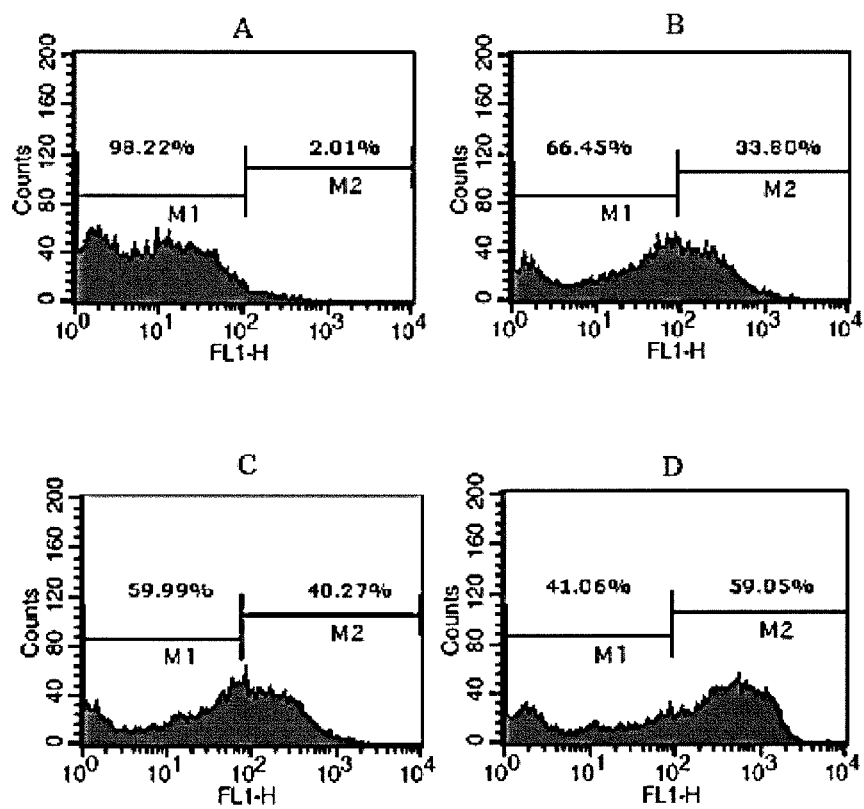
FIG. 5 illustrates effects of the compound of Formula (1a) on apoptosis in HeLa cancer cells.

Results: The vehicle control cells showed 2.01% annexin V positive cells (M2), while cells exposed to compound of Formula (1a) with 0.0003 μM, 0.003 μM and 0.01 μM concentrations for 12 hrs showed respectively 33.80%, 40.27% and 59.05% cells positive for annexin V staining (M2) respectively (as shown in FIG. 5).

Conclusion: This data indicates that, compound of Formula (1a) induces cell death through apoptosis in HeLa cancer cells.

Example 18

Assay

Study of Protein Expression by High Content Screening

Protein expressions of cyclin D, nuclear factor-kappa B (p65) [NFkB (p65)], ribosomal protein S6 (pS6), tumor protein 53 (p53), protein c-jun N-terminal kinase (pJNK), cleaved caspase 9, cleaved caspase 3 and cleaved poly(ADP-ribose) polymerase (PARP) was carried out in HeLa cells [referred to in step 1 of example 16] by Cellomics high content imaging. These primary antibodies were purchased from Santacruz Biotechnology, USA. Briefly $1 \times 10^4$ cells were seeded in 96 well tissue culture grade black plate with transparent bottom (Nunc, USA), and allowed to adhere for 24 h, and then replaced with fresh media, and cells were treated with 0.01 µM, 0.003 µM and 0.0003 µM concentrations of compound of Formula (1) [referred to in step 2 of example 16] and incubated for 1 h and 3 h respectively. After respective time point, cells were fixed with 3.7% formaldehyde (Sigma St. Louis, Mo.) for 10 minutes at RT, followed by permeabilization with 0.15% Triton X-100 (Sigma St. Louis, Mo.) for 10 minutes. Then the cells were blocked with 5% Bovine Serum Albumin for 2 hours. After blocking step, specific primary antibodies were added for 1 h, and primary antibodies of different protein were localized by secondary antibody labeled with Dylight548 (red) (Thermofisher, USA). Following secondary incubation, the nucleus was stained with Hoechst 3342 (blue) (Sigma, USA). Immunofluorescence was determined by scanning the plates on Cellomics Array Scan® VTI HCS Reader (Thermo-Fisher Scientific Inc., Waltham, Mass.). All the data points were analyzed using the Compartmental Analysis bio-algorithm of Cellomics and quantitative data were expressed as % activation in comparison to the untreated cells. 1000 cells were counted for each replicate well and the results were presented as an average±S.E.

The results are summarized in Table 4 and Table 5.

TABLE 4

Effect of the compound of Formula (1a) on p53, pJNK, cleaved caspase 9, cleaved caspase 3 and cleaved PARP expression in HeLa cells, after 3 hours

| Concentration of the compound of Formula (1a) | Fold activation with respect to control cells | | | | |
|---|---|---|---|---|---|
| | P53 | pJNK | Cleaved Caspase 9 | Cleaved Caspase 3 | Cleaved PARP |
| 0.0003 µM | −0.15 | 0.55 | −0.04 | −0.04 | 0.52 |
| 0.003 µM | 0.55 | 0.85 | 0.53 | 0.53 | 1.09 |
| 0.01 µM | 2.27 | 2.42 | 2.22 | 1.62 | 1.51 |

TABLE 5

Effect of the compound of Formula (1a) on cyclin D, NFkB (p65) and pS6 protein expression in HeLa cells, after 3 hours

| Concentration of the compound of Formula (1a) | Fold down regulation with respect to control cells | | |
|---|---|---|---|
| | Cyclin D | NFkB (p65) | pS6 |
| 0.0003 µM | −0.57 | −0.46 | −0.42 |
| 0.003 µM | −0.89 | −0.80 | −0.56 |
| 0.01 µM | −3.81 | −1.86 | −1.97 |

Conclusion

Compound of Formula (1a) significantly downregulates protein expression of NFkB (p65), pS6 and cyclin D in cancer cells. It also up-regulates p53, pJNK, cleaved caspase 9 expression, subsequently inducing prominent upregulation of cleaved caspase 3 and cleaved PARP which drives cancer cell towards apoptosis.

Example 19

Biological evaluation of the compound of Formula (1b) and the compounds 1 to 8.

The assays were designed as described above in example 16. The sample preparation for in vitro assay and the determination of $IC_{50}$ values of the compound of Formula (1b) (described in example 8) and the compounds as obtained in examples 9 to 15 [corresponding to compounds 1 to 8] was carried out as described above in example 16.

The $IC_{50}$ value was estimated by visual inspection of the concentration-effect curve. For calculation of mean $IC_{50}$ values over the six cell lines (PC3, MDA MB, HCT116, MCF7, MIAPaCa2, MCF10A) as tested, the geometric mean was selected.

Results are presented in Table 6, given below.

TABLE 6

$IC_{50}$ values of compound of Formula (1b) and the compounds 2 to 9 in different cancer cell lines and normal cells.

| | $IC_{50}$ (µM) in different cancer cell lines | | | | | |
|---|---|---|---|---|---|---|
| Compound | PC3 | MDA MB-231 | HCT116 | MCF7 | MIA PaCa2 | MCF10A |
| Formula (1b) | 0.035 | 0.018 | 0.032 | 0.071 | — | 0.03 |
| Compound 1 | 0.502 | 0.293 | 0.287 | 0.355 | — | 0.247 |
| Compound 2 | 1.045 | 0.800 | 0.635 | 0.826 | — | 0.691 |
| Compound 3 | 0.044 | 0.030 | 0.009 | 0.025 | — | 0.031 |
| Compound 4 | — | 0.2 | 0.170 | 0.030 | — | <0.3 |
| Compound 5 | — | 0.012 | <0.01 | 0.018 | — | <0.01 |
| Compound 6 | 0.998 | 0.343 | 0.284 | 0.977 | — | 0.819 |
| Compound 7 | 0.360 | 0.320 | 0.257 | 0.843 | — | 0.83 |
| Compound 8 | — | — | — | — | 0.043 | 0.045 |

— not tested

Conclusion

The in vitro study revealed that (i) compound of Formula (1b) showed $IC_{50}$ in the range of 0.018 µM to 0.071 µM in different cancer cells; while in normal cells (MCF-10A) it showed an $IC_{50}$ of 0.030 µM; (ii) compounds 1 to 8 showed $IC_{50}$ in the range of 0.009 µM to 1.045 µM in different cancer cells; while in normal cells (MCF-10A) it showed an $IC_{50}$ in the range of <0.010 µM to 0.830 µM.

These data shows that the compound of Formula (1b) and the compounds 1 to 8 are active against highly proliferating cancer cell lines.

We claim:
1. A compound of Formula (1b);

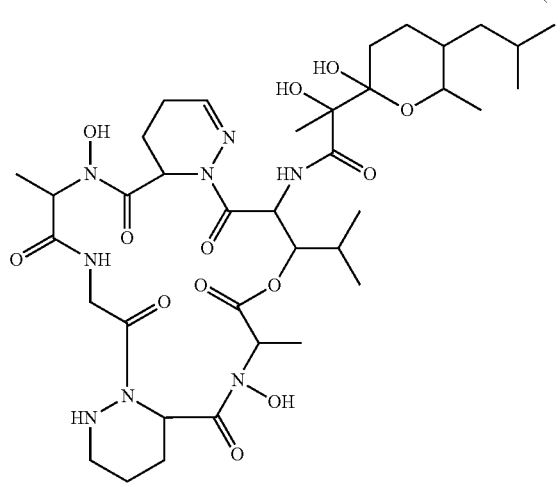

Formula (1b)

characterized by:
a) molecular weight of 824.4,
b) molecular formula $C_{37}H_{60}N_8O_{13}$,
c) IR (KBr): 3342, 3030; 2953, 1752, 1650, 1524, 1421, 1293, 1255 and 1239 cm$^{-1}$,
d) $^1$H NMR spectrum (500 MHz, CDCl$_3$): δ 9.20, 8.00, 7.19, 7.0, 6.18, 6.14, 5.80, 5.41, 5.39, 5.30, 5,10, 4.80 (2), 4.20, 3.70, 3.19, 2.62, 2.27, 2.10, 2.01, 1.98, 1.77, 1.71, 1.62, 1.58, 1.44, 1.40, 1.39, 1.37, 1.20, 1.10, 1.05, 0.96, 0.91, 0.90, 0.86, and 0.85, and
e) $^{13}$C NMR spectrum (75 MHz, CDCl$_3$): δ 176.0, 171.8, 171.7, 170.8, 170.6, 170.3, 168.9, 144.6, 98.8, 79.0, 77.2, 71.7, 53.6, 53.5, 50.6, 49.1, 47.1, 46.4, 42.6, 41.0, 39.8, 29.9, 27.4, 24.7, 24.6, 24.2, 240, 22.1, 21.5. 21.4, 19.8, 19.5, 19.4, 18.1, 17.2, 12.9 and 11.8.

2. A pharmaceutical composition comprising a therapeutically effective amount of the compound as claimed in claim 1 or an isomer or a tautomer, or a pharmaceutically acceptable salt thereof; and a pharmaceutically acceptable excipient, diluent and/or carrier.

3. A compound of Formula (1c):

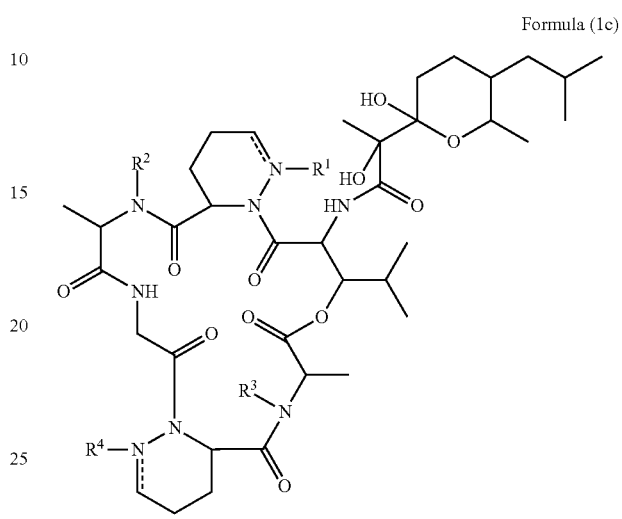

Formula (1c)

wherein: R$^1$ and R$^4$ are H;
R$^2$ is —O(C$_1$-C$_6$)alkyl or —OC(O)(C$_1$-C$_6$)alkyl;
R$^3$ is hydroxy or —O(C$_1$-C$_6$)alkyl;
wherein, (C$_1$-C$_6$)alkyl is unsubstituted or substituted with one or more groups independently selected from the group consisting of —NH$_2$, —NHC(O)(C$_1$-C$_6$)alkyl (C$_6$-C$_{10}$)aryl and —NH-PEG;
or an isomer or a tautomer or a mixture thereof; or a pharmaceutically acceptable salt thereof.

4. The compound according to claim 3, wherein the compound is:

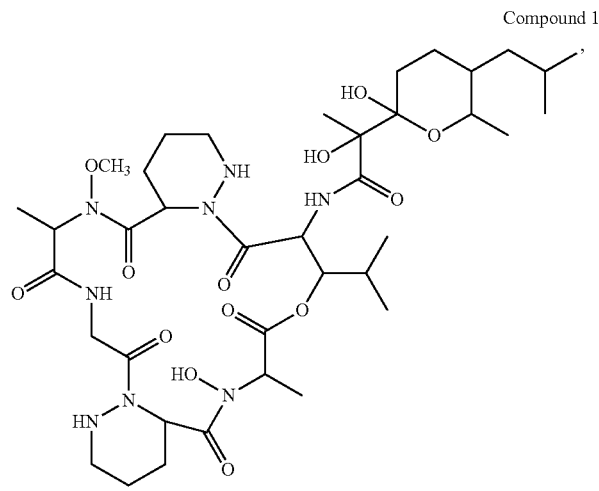

Compound 1

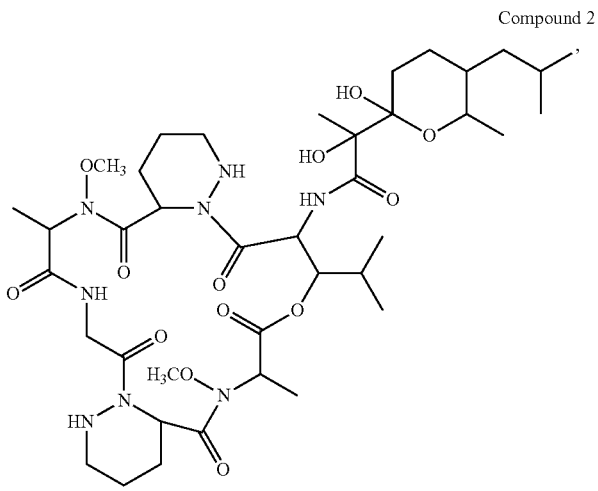

Compound 2

-continued
Compound 3
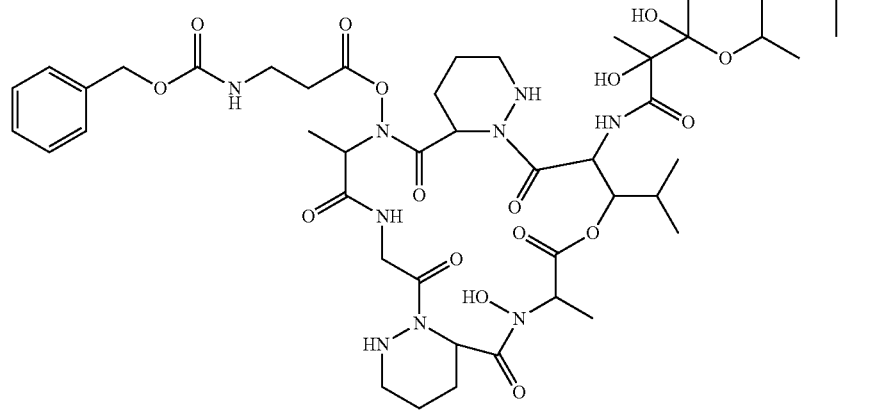
Compound 4
Compound 7
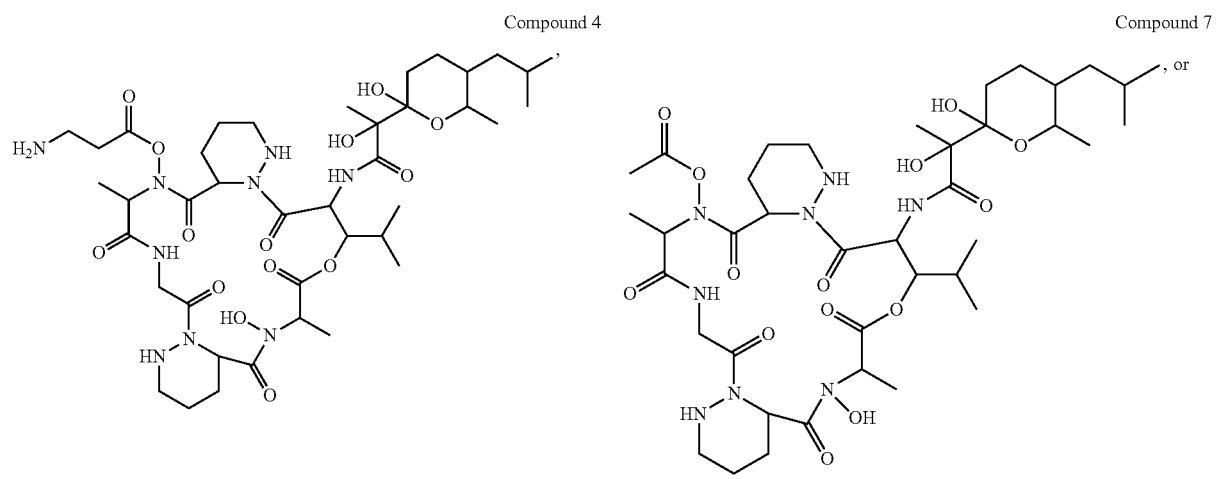
Compound 8
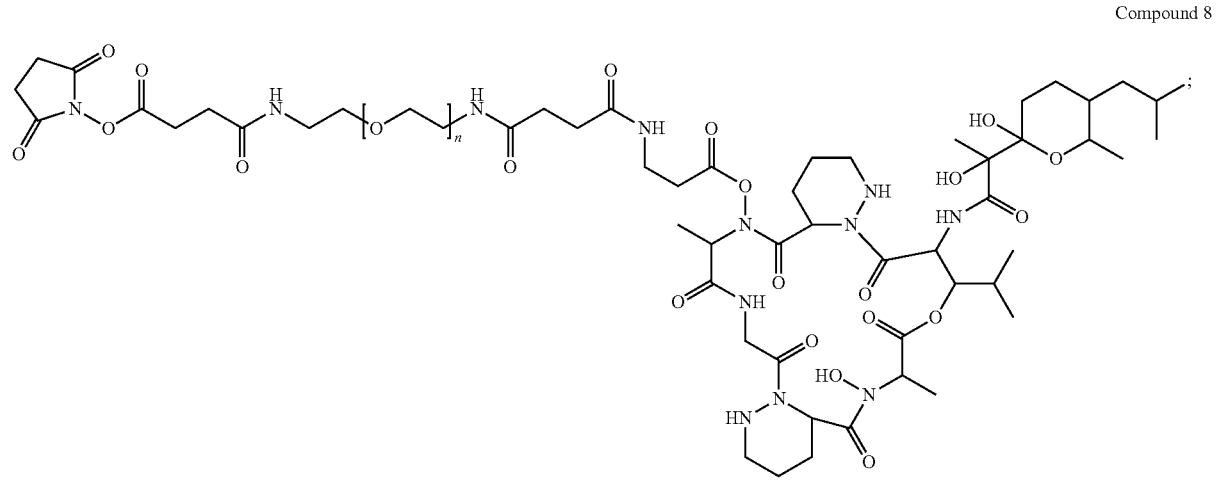

or an isomer or a tautomer or a mixture thereof; or a pharmaceutically acceptable salt thereof.

5. A pharmaceutical composition comprising a therapeutically effective amount of the compound as claimed in claim 4 or an isomer or a tautomer, or a pharmaceutically acceptable salt thereof; and a pharmaceutically acceptable excipient, diluent and/or carrier.

6. A pharmaceutical composition comprising a therapeutically effective amount of the compound as claimed in claim 3 or an isomer or a tautomer, or a pharmaceutically acceptable salt thereof; and a pharmaceutically acceptable excipient, diluent and/or carrier.

7. A compound of Formula (1c):

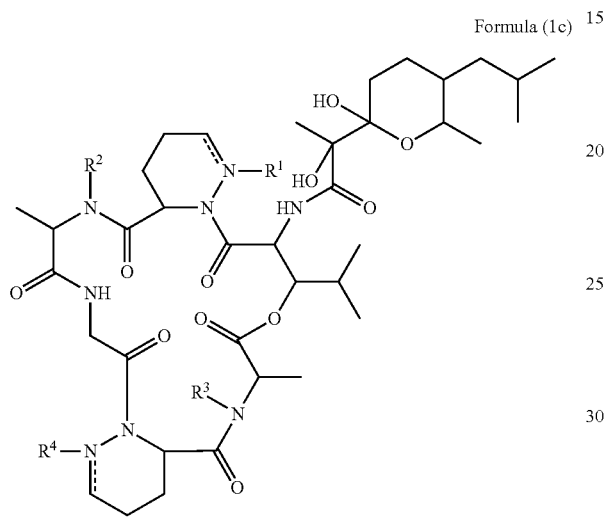

Formula (1c)

wherein: R$^1$ and R$^4$ and H;
R$^1$ and R$^4$ independently represent H or absent;
R$^2$ and R$^3$ are independently selected from H and hydroxy;
----- represents a single bond or a double bond;
with a proviso that if both R$^2$ and R$^3$ are hydroxy, then R$^1$ and R$^4$ are absent and ----- represents a double bond;
or an isomer or a tautomer or a mixture thereof; or a pharmaceutically acceptable salt thereof.

8. The compound according to claim 7, wherein the compound is selected from:

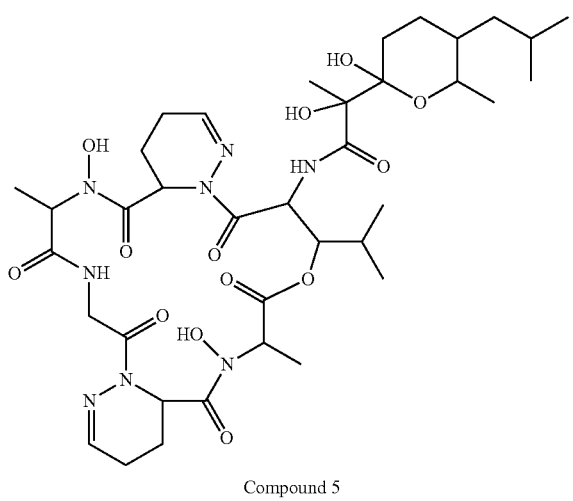

Compound 5 or

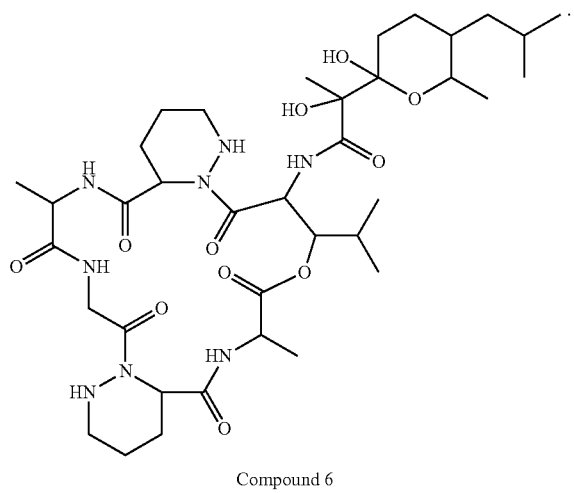

Compound 6

9. A pharmaceutical composition comprising a therapeutically effective amount of the compound as claimed in claim 8 or an isomer or a tautomer, or a pharmaceutically acceptable salt thereof; and a pharmaceutically acceptable excipient, diluent and/or carrier.

10. A pharmaceutical composition comprising a therapeutically effective amount of the compound as claimed in claim 7 or an isomer or a tautomer, or a pharmaceutically acceptable salt thereof; and a pharmaceutically acceptable excipient, diluent and/or carrier.

11. A process for the preparation of the compound as claimed in claim 1, comprising the steps of;
   a) growing the culture no. PM0895172 (MTCC5684), under submerged aerobic conditions in nutrient medium containing sources of carbon, nitrogen and nutrient inorganic salts and/or trace elements, to obtain a culture broth containing the compound of Formula (1b);
   b) isolating the compound of Formula (1b) from the culture broth; and
   c) purifying the compound of Formula (1b).

12. The process according to claim 11, further comprises converting a compound of Formula (1b) into its pharmaceutically acceptable salt.

13. A process for the preparation of the compound as claimed in claim 3, comprising the steps of;
   a) growing the culture no. PM0895172 (MTCC5684), under submerged aerobic conditions in nutrient medium containing sources of carbon, nitrogen and nutrient inorganic salts and/or trace elements, to obtain a culture broth containing the compound of Formula (1c);
   b) isolating the compound of Formula (1c) from the culture broth; and
   c) purifying the compound of Formula (1c).

14. The process according to claim 13, further comprises converting a compound of Formula (1c) into its pharmaceutically acceptable salt.

15. A process for the preparation of the compound as claimed in claim 7, comprising the steps of;
   a) growing the culture no. PM0895172 (MTCC5684), under submerged aerobic conditions in nutrient medium containing sources of carbon, nitrogen and nutrient inorganic salts and/or trace elements, to obtain a culture broth containing the compound of Formula (1c);
b) isolating the compound of Formula (1c) from the culture broth; and
c) purifying the compound of Formula (1c).

16. The process according to claim 15, further comprises converting a compound of Formula (1c) into its pharmaceutically acceptable salt.

* * * * *